(12) United States Patent
Sekioka et al.

(10) Patent No.: US 12,012,679 B2
(45) Date of Patent: Jun. 18, 2024

(54) NONWOVEN FABRIC LAYERED BODY, COMPOSITE LAYERED BODY, AND COVER SHEET

(71) Applicant: MITSUI CHEMICALS ASAHI LIFE MATERIALS CO., LTD., Tokyo (JP)

(72) Inventors: Yusuke Sekioka, Ichihara (JP); Shohei Saita, Yokkaichi (JP); Kosuke Ota, Nagoya (JP); Koichi Shimada, Chiba (JP); Taiichiro Ichikawa, Tokyo (JP)

(73) Assignee: MITSUI CHEMICALS ASAHI LIFE MATERIALS CO., LTD., Tokyo (JP)

( * ) Notice: Subject to any disclaimer, the term of this patent is extended or adjusted under 35 U.S.C. 154(b) by 165 days.

(21) Appl. No.: 17/435,447

(22) PCT Filed: Mar. 4, 2020

(86) PCT No.: PCT/JP2020/009186
§ 371 (c)(1),
(2) Date: Dec. 27, 2021

(87) PCT Pub. No.: WO2020/184335
PCT Pub. Date: Sep. 17, 2020

(65) Prior Publication Data
US 2022/0119998 A1    Apr. 21, 2022

(30) Foreign Application Priority Data

Mar. 8, 2019 (JP) ................................. 2019-042943
Oct. 29, 2019 (JP) ................................. 2019-196708

(51) Int. Cl.
*D04H 1/4391* (2012.01)
*D04H 1/4382* (2012.01)
*D04H 1/544* (2012.01)
*D04H 1/64* (2012.01)

(52) U.S. Cl.
CPC ..... *D04H 1/43918* (2020.05); *D04H 1/43828* (2020.05); *D04H 1/544* (2013.01); *D04H 1/641* (2013.01); *D10B 2321/021* (2013.01); *D10B 2321/022* (2013.01); *D10B 2401/063* (2013.01)

(58) Field of Classification Search
CPC .. D04H 1/43918; B32B 2250/20; B32B 5/271
See application file for complete search history.

(56) References Cited

U.S. PATENT DOCUMENTS

| 5,855,784 | A | * | 1/1999 | Pike | ..................... | B01D 39/163 |
| | | | | | | 442/364 |
| 2002/0010448 | A1 | | 1/2002 | Yoshimasa | | |
| 2004/0067709 | A1 | | 4/2004 | Kishine et al. | | |
| 2007/0021022 | A1 | | 1/2007 | Kishine et al. | | |
| 2015/0173975 | A1 | | 6/2015 | Harumoto et al. | | |
| 2016/0166443 | A1 | | 6/2016 | Arora et al. | | |
| 2017/0119226 | A1 | | 5/2017 | Nakayama et al. | | |
| 2019/0233994 | A1 | * | 8/2019 | Sommer | ............. | D04H 1/5414 |
| 2020/0071867 | A1 | | 3/2020 | Yabe et al. | | |

FOREIGN PATENT DOCUMENTS

| EP | 1 022 125 A1 | 7/2000 |
| JP | H11286863 A | 10/1999 |
| JP | 2005-015964 A | 1/2005 |
| JP | 2005-146503 A | 6/2005 |
| JP | 2008-045241 A | 2/2008 |
| WO | 2002061192 A1 | 8/2002 |
| WO | 2017145999 A1 | 8/2017 |
| WO | 2018/212211 A1 | 11/2018 |

* cited by examiner

*Primary Examiner* — Elizabeth M Imani
(74) *Attorney, Agent, or Firm* — BUCHANAN, INGERSOLL & ROONEY PC

(57) ABSTRACT

A nonwoven fabric layered body includes a first nonwoven fabric layer including a crimped fiber (A), which is a fiber made of a thermoplastic polymer and which has an average crimp diameter of 800 μm or less; and a hydrophilic agent.

16 Claims, No Drawings

NONWOVEN FABRIC LAYERED BODY, COMPOSITE LAYERED BODY, AND COVER SHEET

This application is a 371 of PCT/JP2020/009186, filed Mar. 4, 2020.

TECHNICAL FIELD

The present invention relates to a nonwoven fabric layered body, a composite layered body, and a cover sheet.

BACKGROUND ART

In recent years, nonwoven fabrics are widely used in various applications because of their excellent air breathability and flexibility. For that reason, the nonwoven fabrics require various characteristics in accordance with their applications, and improvements in their characteristics.

For example, a nonwoven fabric (such as atop sheet of an absorbent article) used for a member that comes into direct contact with the skin is required to have excellent flexibility and hydrophilicity. For example, Patent Literature 1 proposes a specific hydrophilic bulky nonwoven fabric composed of thermoplastic fibers. Specific crimped fibers are applied to this hydrophilic bulky nonwoven fabric. Further, Patent Literature 1 discloses that a hydrophilic bulky nonwoven fabric includes or is coated with a water permeable agent.

Patent Literature 2 discloses a nonwoven fabric web, which includes plural continuous spunbonded crimped fibers and plural openings are extended through the nonwoven fabric web, and discloses that the nonwoven fabric web includes an additive for flexibility, a hydrophilic additive, a hydrophobic additive and the like.

[Patent Literature 1] International Publication No. 2017/145999
[Patent Literature 2] US Patent Application Publication No. 2016/0166443

SUMMARY OF INVENTION

Technical Problem

By the way, as a method of imparting hydrophilicity to the nonwoven fabric, a kneading method and a coating method are known. The kneading method is a method of imparting hydrophilicity to the nonwoven fabric by forming the nonwoven fabric with fibers made of a thermoplastic polymer kneaded with an agent for imparting hydrophilicity (hereinafter, the agent for imparting hydrophilicity is referred to as a hydrophilic agent). The coating method is a method in which the hydrophilic agent is adhered to the fiber surface to impart hydrophilicity to the nonwoven fabric.

In a case in which the nonwoven fabric to which the hydrophilic agent is imparted is applied to, for example, the top sheet of a diaper, the hydrophilic agent may be transferred to a member (gather, and the like) that comes into contact with the top sheet of the diaper. For example, if the hydrophilic agent is transferred to the gather and the gather is hydrophilized, liquid leakage may occur in the diaper.

In a case in which the nonwoven fabric to which the hydrophilic agent is imparted is applied to an application involving post-processing (for example, stretching processing, drilling processing) such as a diaper, the hydrophilic agent may be transferred to the processing machine. If the hydrophilic agent continues to migrate to the processing machine for a long period of time, it is considered that corrosion caused by the migration of the hydrophilic agent will occur.

The object of the present disclosure is to provide a nonwoven fabric layered body that is excellent in hydrophilicity and can suppress the migration of a hydrophilic agent when it comes into contact with another member. The object of the present disclosure is to provide a composite layered body that is excellent in hydrophilicity and can suppress the migration of a hydrophilic agent when it comes into contact with another member.

Solution to Problem

The present disclosure related to the following aspects.

<1> A nonwoven fabric layered body, comprising:
a first nonwoven fabric layer including a crimped fiber (A), which is a fiber made of a thermoplastic polymer and which has an average crimp diameter of 800 μm or less; and
a hydrophilic agent.

<2> The nonwoven fabric layered body according to <1>, wherein the first nonwoven fabric layer is an outermost layer, and the average crimp diameter of the crimped fiber (A) is 600 μm or less.

<3> The nonwoven fabric layered body according to <1> or <2>, wherein the thermoplastic polymer comprises an olefin polymer.

<4> The nonwoven fabric layered body according to <3>, wherein the thermoplastic polymer comprises at least one selected from the group consisting of a propylene polymer and an ethylene polymer, as the olefin polymer.

<5> The nonwoven fabric layered body according to any one of <1> to <4>, wherein a width retention rate is 75% or more in a case in which a tensile stress of 0.1 N/mm is applied in an MD direction of the nonwoven fabric layered body.

<6> The nonwoven fabric layered body according to any one of <1> to <5>, wherein a tensile strength at the time of 5% stretching in an MD direction of the nonwoven fabric layered body is 2.2 N/50 mm or more.

<7> The nonwoven fabric layered body according to any one of <1> to <6>, wherein a transfer amount of the hydrophilic agent from the nonwoven fabric layered body to a nonwoven fabric transfer target is 0.015 g/m² or less.

<8> The nonwoven fabric layered body according to any one of <1> to <7>, wherein a ratio (surface water vapor adsorption area/surface nitrogen adsorption area) of a surface water vapor adsorption area obtained by a BET formula of a water vapor adsorption isotherm in a steam adsorption test, with respect to a surface nitrogen adsorption area obtained by a BET formula of a nitrogen adsorption isotherm in a nitrogen adsorption test, is from 1.5 to 9.0.

<9> The nonwoven fabric layered body according to any one of <1> to <8>, wherein the hydrophilic agent comprises at least one selected from the group consisting of a polyhydric alcohol fatty acid ester, a polyoxyalkylene fatty acid ester, and an alkylene oxide adduct of a polyhydric alcohol fatty acid ester.

<10> The nonwoven fabric layered body according to any one of <1> to <9>, further comprising a second nonwoven fabric layered body including:
a crimped fiber (B), which is a fiber made of a thermoplastic polymer and which has a different average crimp diameter from the average crimp diameter of the crimped fiber (A), the average crimp diameter of the crimped fiber (B) being 500 μm or more, or a non-crimped fiber (C), which is a fiber made of a thermoplastic polymer.

<11> The nonwoven fabric layered body according to <10>, wherein the second nonwoven fabric layer comprises the non-crimped fiber (C).

<12> The nonwoven fabric layered body according to <10> or <11>, wherein:
the fiber of the thermoplastic polymer included in the first nonwoven fabric layer and the second nonwoven fabric comprises a propylene polymer,
the propylene polymer is exposed at a surface of the crimped fiber (A) included in the first nonwoven fabric layer,
the propylene polymer is exposed at a surface of the crimped fiber (B) or the non-crimped fiber (C) included in the second nonwoven fabric layer, and
a difference in melting point between the propylene polymer exposed at the surface of the crimped fiber (A) and the propylene polymer exposed at the surface of the crimped fiber (B) or the non-crimped fiber (C) is from −15° C. to +15° C.

<13> The nonwoven fabric layered body according to <12>, wherein the propylene polymer exposed at the surface of the crimped fiber (A) and the propylene polymer exposed at the surface of the crimped fiber (B) or the non-crimped fiber (C) are respectively a propylene/α-olefin copolymer, a mixture of a propylene homopolymer and a propylene/α-olefin copolymer, or a combination thereof.

<14> The nonwoven fabric layered body according to any one of <10> to <13>, wherein the first nonwoven fabric layer is a layer of spunbond nonwoven fabric, the second nonwoven fabric layer is a layer of spunbond nonwoven fabric, the nonwoven fabric layered body has a pressure bonding portion and a non-pressure bonding portion, and an area ratio of the pressure bonding portion is from 7% to 20%.

<15> The nonwoven fabric layered body according to any one of <1> to <14>, further comprising a melt-blown nonwoven fabric layer comprising a fiber made of a thermoplastic polymer.

<16> The nonwoven fabric layered body according to <15>, wherein the thermoplastic polymer in the melt-blown nonwoven fabric layer is a propylene homopolymer having a melt flow rate of 800 g/10 min or more, an average fiber diameter of the fiber in the melt-blown nonwoven fabric layer is less than 3 μm, and a basis weight of the melt-blown nonwoven fabric layer is less than 3 g/m².

<17> The nonwoven fabric layered body according to <15> or <16>, wherein the thermoplastic polymer in the melt-blown nonwoven fabric layer is a propylene/α-olefin copolymer having a melt flow rate of 200 g/10 min or more, or a mixture of a propylene polymer comprising a propylene/α-olefin copolymer, and a basis weight of the melt-blown nonwoven fabric layer is less than 5 g/m².

<18> A composite layered body, comprising the nonwoven fabric layered body according to any one of <1> to <17>.

<19> A cover sheet, comprising the nonwoven fabric layered body according to any one of <14> to <17> or the composite layered body according to <18>.

Advantageous Effects of Invention

According to the present disclosure, a nonwoven fabric layered body that is excellent in hydrophilicity and can suppress the migration of a hydrophilic agent when it comes into contact with another member (also referred to as a migration suppressing effect) is provided. According to the present disclosure, a composite layered body that is excellent in hydrophilicity and can suppress the migration of a hydrophilic agent when it comes into contact with another member is provided.

DESCRIPTION OF EMBODIMENTS

In the present disclosure, numerical ranges indicated using "to" mean a range including the numerical values described before and after "to" as the lower limit value and the upper limit value, respectively.

In the present disclosure, the "step" refers not only to a step that is independent from the other steps, but also to a step that cannot be clearly distinguished from the other steps, as long as the aim of the step is achieved.

In the present disclosure, when there are plural kinds of substances corresponding to each component in a composition, a content of each component in the composition refers to a total content of the plural substances present in the composition, unless otherwise stated.

In the present disclosure, "MD" (Machine Direction) direction refers to the traveling direction of the nonwoven web in the nonwoven fabric manufacturing apparatus. "CD" (Cross Direction) direction refers to the direction perpendicular to the MD direction and parallel to the main surface (a surface orthogonal to the thickness direction of the nonwoven fabric).

In the present disclosure, "include . . . as a main part" means that the target substance is included in the largest amount in the whole. For example, as a ratio to the whole, it is shown that the content ratio of the target substance is 50% by mass or more.

<Nonwoven Fabric Layered Body>

A nonwoven fabric layered body in the present disclosure includes:
a first nonwoven fabric layer including a crimped fiber (A), which is a fiber made of a thermoplastic polymer and which an average crimp diameter of 800 μm or less; and
a hydrophilic agent.

The large average crimp diameter of the crimped fiber (A) means that the degree of the fiber crimping is small. The present inventors found that the migration suppressing effect of a hydrophilic agent included in the nonwoven fabric layered body is preferably exhibited by making the average crimp diameter of the crimped fiber (A) smaller than a specific value. The reason why this migration suppressing effect is preferably exhibited is presumed as follows. In a case in which the average crimp diameter is too large, the migration suppressing effect of the hydrophilic agent included in the nonwoven fabric layered body is low due to small degree of the fiber crimping. On the other hand, in a case in which the average crimp diameter is low, the migration suppressing effect of the hydrophilic agent is exhibited due to large degree of the fiber crimping.

The first nonwoven fabric layer includes a crimped fiber (A) that is a fiber made of a thermoplastic polymer. Further, the average crimp diameter of the crimped fiber (A) is 800 μm or less, preferably 700 μm or less, more preferably 600 μm or less, further preferably 550 μm or less, particularly preferably 500 μm or less, and extremely preferably 400 μm or less. In a case in which the average crimp diameter of the crimped fiber (A) is 800 μm or less, a nonwoven fabric layered body that is excellent in hydrophilicity and can suppress the migration of a hydrophilic agent when it comes into contact with another member is obtained. From the viewpoint of improving a cushioning property of a crimped portion and improving the flexibility, the average crimp diameter of the crimped fiber (A) is preferably 200 µm or more, more preferably 220 µm or more, further preferably 250 µm or more, and particularly preferably 270 µm or more.

In the present disclosure, a crimp diameter represents the size of the crimp in a crimped fiber that forms one round or more crimps, and the average crimp diameter represents the average value of the crimp size. In the present disclosure, the average crimp diameter is measured as follows.

First, a measurement sample is collected from a nonwoven fabric layer to be measured. Next, the measurement sample is placed on the microscope stage of the optical microscope ("ECLIPSE E400" manufactured by Nikon Corporation). Then, the surface (flat surface) of the nonwoven fabric is observed at a magnification of 4 times, and among the crimped fibers, the crimped fibers having a crimped shape of a semicircle or more are randomly selected at 50 points. Then, the diameters of the selected crimped fibers are measured by the image analysis software "Pixs2000" attached to the optical microscope. The diameters of the crimped fibers are measured by selecting three points on the circumference using the diameter measurement function of the image analysis software. The diameters of the crimped fibers are measured at 50 points, and the average value is calculated to obtain the average crimp diameter.

The nonwoven fabric layered body in the present disclosure includes a second nonwoven fabric layered body. The second nonwoven fabric layer is preferably a layer of a nonwoven fabric including a fiber made of a thermoplastic polymer. The second nonwoven fabric layer is not particularly limited, and for example, may be a layer of a conventionally known nonwoven fabric.

The second nonwoven fabric layer may be a layer of a nonwoven fabric including a spunbond nonwoven fabric, a melt-blown nonwoven fabric, a card type air-through nonwoven fabric, an air-laid nonwoven fabric, a needle punch type spunbond nonwoven fabric, a wet nonwoven fabric, a dry pulp nonwoven fabric, a flashspun nonwoven fabric, a spread nonwoven fabric or the like.

The second nonwoven fabric layer preferably includes a crimped fiber (B) that has a different average crimp diameter from the average crimp diameter of the crimped fiber (A), the average crimp diameter of the crimped fiber (B) being 500 µm or more, or a non-crimped fiber (C). In a case in which a hydrophilic agent is included in a nonwoven fabric made of a crimped fiber in order to make a nonwoven fabric with both flexibility and hydrophilicity, the nonwoven fabric tends to shrink in the CD direction. On the other hand, since the nonwoven fabric layered body in the present disclosure includes the aforementioned crimped fiber (B) or non-crimped fiber (C), when manufacturing the nonwoven fabric layered body, shrinkage in the CD direction is suppressed and stable production is possible. Therefore, the nonwoven fabric layered body including the nonwoven fabric layered body tends to have excellent dimensional stability.

The second nonwoven fabric layer may be a layer of a nonwoven fabric including a non-crimped fiber (C) as a main part that is a fiber made of a thermoplastic polymer. In a case in which the second nonwoven fabric layer is a layer of a nonwoven fabric including a non-crimped fiber (C) as a main part that is a fiber made of a thermoplastic polymer, the average crimp diameter of the crimped fiber (A) is preferably 700 µm or less, more preferably 600 µm or less, further preferably 550 µm or less, and particularly preferably 500 µm or less. Further, in a case in which the second nonwoven fabric layer is a layer of a nonwoven fabric including a non-crimped fiber (C) as a main part that is a fiber made of a thermoplastic polymer, the first nonwoven fabric layer may be an outermost layer. In this case, the average crimp diameter of the crimped fiber (A) is preferably 600 µm or less, more preferably 550 µm or less, and further preferably 500 µm or less. In a case in which the nonwoven fabric layered body in the present disclosure has such a layered structure, the nonwoven fabric layered body that is excellent in hydrophilicity, suppresses the migration of a hydrophilic agent when it comes into contact with another member, and has excellent dimensional stability is more easily obtained.

In a case in which the second nonwoven fabric layer is a layer of a nonwoven fabric including a non-crimped fiber (C) as a main part, the second nonwoven fabric layer may include another fiber other than the non-crimped fiber (C). Examples of another fiber include the aforementioned crimped fiber (B), and a crimped fiber other than the crimped fiber (B). Another fiber may be a long fiber, or may be a short fiber.

In the present disclosure, "short fiber" means a fiber with an average fiber length of 200 mm or less.

The second nonwoven fabric layer may be a layer of a nonwoven fabric including the non-crimped fiber (C) and another fiber other than the non-crimped fiber (C), and including a spunbond nonwoven fabric, a melt-blown nonwoven fabric, a card type air-through nonwoven fabric, an air-laid nonwoven fabric, a needle punch type spunbond nonwoven fabric, a wet nonwoven fabric, a dry pulp nonwoven fabric, a flashspun nonwoven fabric, a spread nonwoven fabric or the like.

The second nonwoven fabric layer may be a layer of a nonwoven fabric including the aforementioned crimped fiber (B) as a main part that is a fiber made of a thermoplastic polymer. In a case in which the second nonwoven fabric layer is a layer of a nonwoven fabric including the crimped fiber (B) as a main part that is a fiber made of a thermoplastic polymer, from the viewpoint of exhibiting both excellent flexibility and excellent dimensional stability, the average crimp diameter of the crimped fiber (B) is preferably 500 µm or more, more preferably 550 µm or more, further preferably 600 µm or more, and particularly preferably 650 µm or more. The average crimp diameter of the crimped fiber (B) is preferably 1500 µm or less, and more preferably 1000 µm or less. In a case in which the average crimp diameters of the crimped fiber (A) and the crimped fiber (B) are different from each other, and the average crimped diameters of the crimped fiber (A) and the crimped fiber (B) are in the above range, the nonwoven fabric layered body that is excellent in hydrophilicity, suppresses the migration of a hydrophilic agent when it comes into contact with another member, and has excellent dimensional stability is more easily obtained. In a case in which the second nonwoven fabric layer includes the crimped fiber (B), a difference between the average crimp diameters of the crimped fiber (A) and the crimped fiber (B) is not particularly limited, and for example may be 100 µm or more.

In a case in which the second nonwoven fabric layer may be a layer of a nonwoven fabric including the aforementioned crimped fiber (B) as a main part, the second nonwoven fabric layer may include another fiber other than the crimped fiber (B). Examples of another fiber include a crimped fiber other than the crimped fiber (B) and the aforementioned non-crimped fiber (C). Another fiber may be a long fiber, or may be a short fiber.

The second nonwoven fabric layer may be a layer of a nonwoven fabric including the crimped fiber (B) and another fiber other than the crimped fiber (B), and including a spunbond nonwoven fabric, a melt-blown nonwoven fabric, a card type air-through nonwoven fabric, an air-laid nonwoven fabric, a needle punch type spunbond nonwoven fabric, a wet nonwoven fabric, a dry pulp nonwoven fabric, a flashspun nonwoven fabric, a spread nonwoven fabric or the like.

In a case in which the second nonwoven fabric layer is a layer of a nonwoven fabric including the crimped fiber (B) as a main part that is a fiber made of a thermoplastic polymer, the first nonwoven fabric layer is a outermost layer in the nonwoven fabric layered body. In this case, the average crimp diameter of the crimped fiber (A) included in the first nonwoven fabric layer is preferably 600 µm or less, more preferably 550 µm or less, further preferably 500 µm or less, and particularly preferably 400 µm or less. By making the nonwoven fabric layered body such a structure, the nonwoven fabric layered body that is excellent in hydrophilicity, suppresses the migration of a hydrophilic agent when it comes into contact with another member, and has excellent dimensional stability is more easily obtained.

The nonwoven fabric layered body may have plural first nonwoven fabric layers or may have plural second nonwoven fabric layers. For example, the nonwoven fabric layered body may have a layer structure of first nonwoven fabric layer/first nonwoven fabric layer/second nonwoven fabric layer, may have a layer structure of first nonwoven fabric layer/second nonwoven fabric layer/first nonwoven fabric layer, may have a layer structure of first nonwoven fabric layer/second nonwoven fabric layer/second nonwoven fabric layer, may have a layer structure of first nonwoven fabric layer/first nonwoven fabric layer/first nonwoven fabric layer/second nonwoven fabric layer, may have a layer structure of first nonwoven fabric layer/first nonwoven fabric layer/second nonwoven fabric layer/second nonwoven fabric layer, may have a layer structure of first nonwoven fabric layer/first nonwoven fabric layer/second nonwoven fabric layer/first nonwoven fabric layer, may have a layer structure of first nonwoven fabric layer/second nonwoven fabric layer/first nonwoven fabric layer/first nonwoven fabric layer/second nonwoven fabric layer, may have a layer structure of first nonwoven fabric layer/second nonwoven fabric layer/second nonwoven fabric layer/second nonwoven fabric layer, or may have a layer structure of first nonwoven fabric layer/second nonwoven fabric layer/second nonwoven fabric layer/first nonwoven fabric layer. Further, the nonwoven fabric layered body in the present disclosure may include a melt-blown nonwoven fabric layer described below, for example, a melt-blown nonwoven fabric layer may be provided on the first nonwoven fabric layer, on the second nonwoven fabric layer, between two first nonwoven fabric layers, between two second nonwoven fabric layers, or between the first nonwoven fabric layer and the second nonwoven fabric layer. The nonwoven fabric layered body in the present disclosure may have plural melt-blown nonwoven fabric layers described below.

In the nonwoven fabric layered body in the present disclosure, the first nonwoven fabric layer is preferably a layer of a spunbond nonwoven fabric, or in a case in which the aforementioned nonwoven fabric layered body is provided with the second nonwoven fabric layer, it is preferable that the first nonwoven fabric layer is a layer of a spunbond nonwoven fabric, and the second nonwoven fabric layer is a layer of a spunbond nonwoven fabric.

The fiber (that is, the crimped fiber (A) included in the first nonwoven fabric layer, and the crimped fiber (B) or the non-crimped fiber (C) included in the second nonwoven fabric layer) made of a thermoplastic polymer included in the first nonwoven fabric layer and the second nonwoven fabric layer is not particularly limited as long as it is a fiber that can constitute a nonwoven fabric. Examples of the thermoplastic polymer constituting the fiber include an olefin polymer, a polyester polymer, a polyamide polymer, and a thermoplastic polymer composition including these plural polymers. In the present disclosure, the thermoplastic polymer is a concept that includes the thermoplastic polymer composition.

In a case in which another fiber other than the crimped fiber (A) is included in the first nonwoven fabric layer, or in a case in which another fiber other than the crimped fiber (B) or the non-crimped fiber (C) is included in the second nonwoven fabric layer, examples of thermoplastic polymer constituting other fibers each independently include an olefin polymer, a polyester polymer, a polyamide polymer, and a thermoplastic polymer composition including these plural polymers.

The olefin polymer is a polymer including a structural unit derived from an olefin as a main part, the polyester polymer is a polymer including a structural unit derived from polyester, and the polyamide polymer is a polymer including a structural unit derived from polyamide. It is preferable that the thermoplastic polymer includes the olefin polymer, and it is more preferable that the thermoplastic polymer includes at least one selected from the group consisting of a propylene polymer and an ethylene polymer as the olefin polymer.

The propylene polymer is a polymer mainly composed of a structural unit derived from propylene, a concept that includes a propylene homopolymer and a copolymer (propylene/α-olefin random copolymer) of propylene and an α-olefin other than propylene. For example, the propylene polymer may be either a propylene homopolymer or a copolymer of propylene and an α-olefin other than propylene, or may include both. For example, the propylene/α-olefin random copolymer is preferably a random copolymer of propylene and one or more than one α-olefins having 2 to 10 carbon atoms other than propylene, and more preferably a random copolymer of propylene and one or, two or more α-olefins having 2 to 8 carbon atoms other than propylene. From the viewpoint of excellent flexibility, Examples of a preferable α-olefin copolymerizing with propylene include ethylene, 1-butene, 1-pentene, 1-hexene, 1-octene, 1-decene, 3-methyl-1-butene, 3-methyl-1-pentene, 3-ethyl-1-pentene, 4-methyl-1-pentene, and 4-methyl-1-hexene. Examples of the propylene/α-olefin random copolymer include a propylene/ethylene random copolymer, and a propylene/ethylene/1-butene random copolymer. A content of a structural unit derived from α-olefin in the propylene/α-olefin random copolymer is not particular limited, and for example, is preferably from 1 mol % to 10 mol %, and more preferably from 1 mol % to 5 mol %. The propylene polymer may include two or more different propylene polymers, or may include the propylene polymer and the ethylene polymer.

In the present disclosure, in a case in which a content of a structural unit derived from propylene and a content of a structural unit derived from ethylene are the same in the copolymer of propylene and an α-olefin other than propylene, such a copolymer is classified as the propylene polymers The ethylene polymer is a polymer mainly composed of a structural unit derived from ethylene, a concept that includes an ethylene homopolymer and a copolymer of ethylene and an α-olefin other than ethylene. For example, it may be either the ethylene homopolymer or the copolymer of ethylene and an α-olefin other than ethylene (ethylene/α-olefin random copolymer). For example, the ethylene/α-olefin random copolymer is preferably a random copolymer of ethylene and one or more than one α-olefins having 2 to 10 carbon atoms other than ethylene. From the viewpoint of excellent flexibility, Examples of an α-olefin copolymerizing with ethylene include propylene, 1-butene, 1-pentene, 1-hexene, 1-octene, 1-decene, 3-methyl-1-butene, 3-methyl-1-pentene, 3-ethyl-1-pentene, 4-methyl-1-pentene, and 4-methyl-1-hexene. Examples of the ethylene/α-olefin random copolymer includes an ethylene/propylene random copolymer and an ethylene/1-butene random copolymer. The ethylene polymer may include two or more different ethylene polymers, or may include the ethylene polymer and the propylene polymer.

A density of an ethylene/α-olefin random copolymer is preferably from 900 kg/m³ to 980 kg/m³, from the viewpoint of spinnability, more preferably from 910 kg/m³ to 980 kg/m³, and further preferably from 950 kg/m³ to 980 kg/m³. From the viewpoint of crimp diameter, the aforementioned density is preferably from 900 kg/m³ to 960 kg/m³, and more preferably from 900 kg/m³ to 940 kg/m³. From the viewpoint of a balance between spinnability and crimp diameter, the aforementioned density is preferably from 910 kg/m³ to 940 kg/m³. For example, a melting point and the density of the ethylene/α-olefin random copolymer can be respectively adjusted to the aforementioned numeral range by adjusting a content of/α-olefin included in the ethylene/α-olefin random copolymer. In the ethylene/α-olefin random copolymer, it is known that there is a correlation between the density and the melting point.

A melting point (Tm) of the propylene polymer is preferably 125° C. or more, and more preferably from 125° C. to 165° C. From the viewpoint of spinnability, a melt flow rate (MFR) (ASTM D1238, 230° C., and load: 2,160 g) of the propylene polymer is preferably from 10 g/10 min to 100 g/10 min, and more preferably from 20 g/10 min to 70 g/10 min.

From the viewpoint of spinnability, a melt flow rate (MFR) (ASTM D1238, 230° C., and load: 2,160 g) of the ethylene polymer is preferably from 1 g/10 min to 100 g/10 min, and more preferably from 20 g/10 min to 70 g/10 min.

In a case in which the fiber made of the thermoplastic polymer included in the second nonwoven fabric layer is the non-crimped fiber (C), the non-crimped fiber (C) may be a fiber including one kind of the thermoplastic polymer, or may be a fiber including two or more kinds of the thermoplastic polymers. The non-crimped fiber (C) preferably includes the propylene polymer.

In a case in which the fiber made of the thermoplastic polymer included in the second nonwoven fabric layer is the crimped fiber (B), the crimped fiber (A) made of the thermoplastic polymer included in the first nonwoven fabric layer, and the crimped fiber (B) may be a fiber including one kind of the thermoplastic polymer, or may be a composite fiber including two or more kinds of the thermoplastic polymers. In a case in which each of the crimped fiber (A) made of the thermoplastic polymer included in the first nonwoven fabric layer and the crimped fiber (B) made of the thermoplastic polymer included in the second nonwoven fabric layer is a composite fiber, the composite fibers may be, for example, a side-by-side type, a concentric core sheath type or an eccentric core sheath type. The eccentric core sheath type composite fiber may be an exposed type in which the core portion is exposed at the surface, or a non-exposed type in which the core portion is not exposed at the surface.

Each of the crimped fiber (A) made of the thermoplastic polymer included in the first nonwoven fabric layer and the crimped fiber (B) made of the thermoplastic polymer included in the second nonwoven fabric layer is preferably a composite fiber including the propylene polymer, more preferably a crimped composite fiber including the propylene polymer, and further preferably an eccentric core sheath type crimped composite fiber. By using the composite fiber including the propylene polymer, the nonwoven fabric layered body that is excellent in hydrophilicity and suppresses the migration of a hydrophilic agent when it comes into contact with another member and exhibits both flexibility and dimensional stability is more easily obtained.

It is preferable that the fibers made of the thermoplastic polymer included in the first nonwoven fabric layer and the second nonwoven fabric layer are the fibers including the propylene polymer, the propylene polymer is exposed at the surface of the crimped fiber (A) included in the first nonwoven fabric layer and the propylene polymer is exposed at the surface of the crimped fiber (B) or the non-crimped fiber (C) included in the second nonwoven fabric layer, and a difference in a melting point between the propylene polymer exposed at the surface of the crimped fiber (A) and the propylene polymer exposed at the surface of the crimped fiber (B) or the non-crimped fiber (C) is from −15° C. to +15° C.

From the viewpoint that when embossed at a high temperature, a polymer portion on a low melting point side becomes relatively soft, and from the viewpoint that when embossed at a low temperature, a polymer portion on a high melting point side is preferably thermally entangled and sufficient strength can be obtained, it is preferable to reduce a difference in a melting point between the propylene polymer exposed at the surface of the crimped fiber (A) included in the first nonwoven fabric layer and the propylene polymer exposed at the surface of the crimped fiber (B) or the non-crimped fiber (C) included in the second nonwoven fabric layer. In order to make the polymer portion easier to be thermally entangled, the propylene polymer exposed at the surface of the crimped fiber (A) included in the first nonwoven fabric layer and the propylene polymer exposed at the surface of the crimped fiber (B) or the non-crimped fiber (C) included in the second nonwoven fabric layer may be a propylene/α-olefin copolymer, a mixture of a propylene homopolymer and a propylene/α-olefin copolymer, or a combination thereof.

A melting point of the propylene/α-olefin random copolymer as the propylene/α-olefin copolymer can be measured using a differential scanning calorimetry (DSC).

With the differential scanning calorimeter (DSC), raise the temperature to a temperature about 50° C. higher than the temperature that gives the extreme value of the melting endothermic curve when the temperature is raised at a heating rate of 10° C./min, and hold at this temperature for 10 minutes. Then, the temperature is cooled to 30° C. at a temperature dropping rate of 10° C./min, and the melting curve is measured again when the temperature is raised to a predetermined temperature at a temperature rising rate of 10° C./min. From the melting curve, according to the method of ASTM D3418, the temperature (Tp) that gives the extreme value of the melting endothermic curve can be obtained, and the endothermic peak of the peak temperature can be obtained as the melting point (Tm).

In a case in which each of the crimped fiber (A) and the crimped fiber (B) is a composite fiber, "exposed at the surface of the crimped fiber" refers to the side with more exposed portion at the surface of the composite fiber. "The side with more exposed portion at the surface" means the side where the thermoplastic polymer is more exposed in the composite fiber. In the present disclosure, the side with more exposed portion at the surface is collectively called a sheath portion. Further, the side with less exposed portion at the surface is collectively called a core portion. The composite fiber having the largest amount of exposed portion at the surface (that is, the composite fiber having the largest sheath portion) is a non-exposed type composite fiber since the exposure of the core portion is the smallest.

In a case in which the composite fiber is a core sheath type, a mass ratio (core portion/sheath portion) of the sheath portion and the core portion is, for example, preferably from 95/5 to 5/95, more preferably from 90/10 to 10/90, and further preferably from 90/10 to 40/60. The mass ratio of the sheath portion and the core portion can be selected depending on the type of resin used for the sheath portion and the core portion and the target average crimp diameter.

An average fiber diameter of a fiber made of the thermoplastic polymer included in the first nonwoven fabric layer and the second nonwoven fabric layer is preferably 5 μm or more, and more preferably 7 μm or more. The aforementioned average fiber diameter is preferably 25 μm or less, and more preferably 20 μm or less. In the present disclosure, the average fiber diameter is measured as follows. From the obtained nonwoven fabric layered body, 10 test pieces of 10 mm×10 mm are sampled, and the diameter of the fiber is read to the first decimal place in μm units at a magnification of 20 times using an ECLIPSE E400 microscope manufactured by Nikon Corporation. The diameters of 20 arbitrary points for each test piece are measured and the average value is calculated. The same is performed for each nonwoven fabric layer, for example, a layer of a spunbond nonwoven fabric layer, a melt-blown nonwoven fabric layer, and the like.

The nonwoven fabric layered body in the present disclosure, it is preferable to further include a melt-blown nonwoven fabric layer including a fiber made of a thermoplastic polymer.

From the viewpoint of a barrier property, an average fiber diameter of the fiber included in the melt-blown nonwoven fabric layer is preferably less than 3.0 μm, more preferably 2.8 μm or less, and further preferably 2.6 μm or less.

In the average fiber diameter of the fiber included in the melt-blown nonwoven fabric layer, a lower limit thereof is not particularly limited as long as the lower limit is more than 0 μm, the lower limit is preferably 0.5 μm or more.

The method for measuring the average fiber diameter of the melt-blown fiber is as described above except that the magnification of the microscope is appropriately adjusted (for example, set to 1,000 times and observed with a scanning electron microscope).

Examples of the thermoplastic polymer constituting the melt-blown nonwoven fabric layer include an olefin polymer such as a high pressure low density polyethylene, a linear low density polyethylene (so-called LLDPE), a high density polyethylene, a propylene polymer (a propylene homopolymer, a polypropylene random copolymer, a propylene/α-olefin copolymer, etc.), poly 1-butene, poly 4-methyl-1-pentene, an ethylene/propylene random copolymer, an ethylene/1-butene random copolymer, or a propylene/1-butene random copolymer, which is a homopolymer or a copolymer of α-olefins such as ethylene, propylene, 1-butene, 1-pentene, 1-hexene, 1-octene, 1-decene, 3-methyl-1-butene, 3-methyl-1-pentene, 3-ethyl-1-pentene, 4-methyl-1-pentene and 4-methyl-1-hexene; polyester such as polyethylene terephthalate, polybutylene terephthalate, or polyethylene naphthalate; a polyamide polymer such as nylon-6, nylon-66, or polymethoxylen adipamide; polyvinyl chloride, polyimide, an ethylene/vinyl acetate copolymer, polyacrylonitrile, polycarbonate, polystyrene, an ionomer, thermoplastic polyurethane, or a mixture thereof.

Among the above, as the thermoplastic polymer constituting the melt-blown nonwoven fabric layer, the olefin polymer is preferable, and the propylene polymer is more preferable.

The propylene polymers constituting the melt-blown nonwoven fabric layer are preferably a propylene homopolymer and a propylene/α-olefin copolymer that is a copolymer of propylene and one or more α-olefins (excluding propylene) having two or more carbon atoms. One or more α-olefins (excluding propylene) having 2 or more carbon atoms are preferably one or more α-olefins (for example, ethylene, 1-butene, 1-pentene, 1-hexene, 1-octene, 1-decene, 3-methyl-1-butene, 3-methyl-1-pentene, 3-ethyl-1-pentene, 4-methyl-1-pentene, 4-methyl-1-hexene) having 2 to 10 carbon atoms, and more preferably one or more α-olefins having 2 to 8 carbon atoms.

A melting point (Tm) of the propylene homopolymer is preferably 155° C. or more, and more preferably from 157° C. to 165° C.

A content of a structural unit derived from an α-olefin of the propylene/α-olefin copolymer with respect to all structural units is preferably from 0.5% by mass to 25% by mass, and more preferably from 1.0% by mass to 20% by mass.

The thermoplastic polymer may be a mixture of plural propylene polymers. Examples of the aforementioned mixture include a mixture of a propylene/α-olefin copolymer and a propylene homopolymer, a mixture of a propylene/α-olefin copolymer and a propylene polymer wax, and a mixture of three types of a propylene/α-olefin copolymer, a propylene homopolymer, and a propylene polymer wax. The propylene polymer wax is a propylene polymer having a relatively low molecular weight, that is, a wax-like propylene polymer.

The weight average molecular weight (Mw) of the propylene polymer wax is preferably from 400 to 30,000, more preferably from 400 to 25,000, and further preferably from 1,000 to 10,000.

The molecular weight and molecular weight distribution of the wax are measured using the GPC method.

Measurement is performed under the following conditions using commercially available monodisperse standard polystyrene as the standard.

Equipment: Gel permeation chromatograph Alliance GPC2000 type (manufactured by Waters Corporation)
Solvent: o-dichlorobenzene
Column: TSKgel column (manufactured by Tosoh Corporation)×4
Flow velocity: 1.0 ml/min
Sample: 0.3% o-dichlorobenzene solution
Temperature: 140° C.

When the Mw of the propylene polymer wax is within the above range, it becomes easier to make the fibers constituting the melt-blown nonwoven fabric thinner, and it is possible to further suppress the generation of shots when the molten fibers are discharged.

The propylene polymer wax preferably has a softening point of 90° C. or higher, more preferably 100° C. or higher, as measured according to JIS K2207: 1996.

When the softening point is 90° C. or higher, the heat resistance stability during heat treatment, use, etc. can be further improved, and as a result, the heat resistance of the melt-blown nonwoven fabric can be further improved.

The upper limit of the softening point is not particularly limited, and for example, 168° C. or lower.

Examples of the propylene polymer wax include a propylene homopolymer, a copolymer of propylene and an α-olefin having 2 or 4 to 20 carbon atoms.

a melt flow rate (MFR) (ASTM D1238, 230° C., and load: 2,160 g) of the propylene polymer constituting the melt-blown nonwoven fabric is, for example, from the viewpoint of thinning the fibers and obtaining a flexible nonwoven fabric layered body, preferably 200 g/10 min or more, and more preferably 800 g/10 min or more. From the viewpoint of spinning stability, the aforementioned melt flow rate is preferably 2000 g/10 min or less, and more preferably 1600 g/10 min or less.

From the viewpoint of flexibility after forming the nonwoven fabric layered body, a basis weight of the melt-blown nonwoven fabric layer is preferably less than 5 g/m$^2$, and more preferably less than 3 g/m$^2$. The lower limit of the basis weight of the melt-blown nonwoven fabric layer is not particularly limited, and for example, from the viewpoint of a barrier property, is preferably 0.2 g/m$^2$ or more, is more preferably 0.5 g/m$^2$ or more, and further preferably 0.7 g/m$^2$ or more.

The measurement method of the basis weight in the present disclosure is as described in Examples described later.

In the nonwoven fabric layered body in the present disclosure, it is preferable that the thermoplastic polymer included in the melt-blown nonwoven fabric layer is a propylene homopolymer with the melt flow rate of 800 g/10 min or more, the average fiber diameter of the fibers included in the melt-blown nonwoven fabric layer is less than 3 μm, and the basis weight of the melt-blown nonwoven fabric layer is less than 3 g/m$^2$. As a result, flexibility after forming the nonwoven fabric layered body tends to be excellent.

In the nonwoven fabric layered body in the present disclosure, it is preferable that the thermoplastic polymer included in the melt-blown nonwoven fabric layer is a propylene/α-olefin copolymer having a melt flow rate of 200 g/10 min or more, or a mixture of a propylene polymer including a propylene/α-olefin copolymer, and the basis weight of the melt-blown nonwoven fabric layer is less than 5 g/m$^2$. As a result, flexibility after forming the nonwoven fabric layered body tends to be excellent.

In the nonwoven fabric layered body in the present disclosure, the first nonwoven fabric layer is preferably a layer of a spunbond nonwoven fabric. The nonwoven fabric layered body in the present disclosure may include the second nonwoven fabric layer that is a layer of a spunbond nonwoven fabric, a melt-blown nonwoven fabric layer or the like. In this case, examples of a preferable aspect of the nonwoven fabric layered body include first nonwoven fabric layer/first nonwoven fabric layer/melt-blown nonwoven fabric layer/first nonwoven fabric layer, first nonwoven fabric layer/melt-blown nonwoven fabric layer/first nonwoven fabric layer/first nonwoven fabric layer, first nonwoven fabric layer/first nonwoven fabric layer/melt-blown nonwoven fabric layer/second nonwoven fabric layer, first nonwoven fabric layer/melt-blown nonwoven fabric layer/first nonwoven fabric layer/second nonwoven fabric layer, first nonwoven fabric layer/second nonwoven fabric layer/melt-blown nonwoven fabric layer/first nonwoven fabric layer, first nonwoven fabric layer/melt-blown nonwoven fabric layer/second nonwoven fabric layer/first nonwoven fabric layer, first nonwoven fabric layer/second nonwoven fabric layer/second nonwoven fabric layer, first nonwoven fabric layer/melt-blown nonwoven fabric layer/second nonwoven fabric layer/second nonwoven fabric layer, first nonwoven fabric layer/first nonwoven fabric layer/melt-blown nonwoven fabric layer/first nonwoven fabric layer/first nonwoven fabric layer, first nonwoven fabric layer/first nonwoven fabric layer/melt-blown nonwoven fabric layer/first nonwoven fabric layer/second nonwoven fabric layer, first nonwoven fabric layer/first nonwoven fabric layer/melt-blown nonwoven fabric layer/first nonwoven fabric layer/melt-blown nonwoven fabric layer, first nonwoven fabric layer/melt-blown nonwoven fabric layer/first nonwoven fabric layer/first nonwoven fabric layer/first nonwoven fabric layer, first nonwoven fabric layer/melt-blown nonwoven fabric layer/first nonwoven fabric layer/first nonwoven fabric layer/second nonwoven fabric layer, first nonwoven fabric layer/melt-blown nonwoven fabric layer/first nonwoven fabric layer/first nonwoven fabric layer/melt-blown nonwoven fabric layer, first nonwoven fabric layer/melt-blown nonwoven fabric layer/first nonwoven fabric layer/first nonwoven fabric layer, first nonwoven fabric layer/first nonwoven fabric layer/melt-blown nonwoven fabric layer/second nonwoven fabric layer/first nonwoven fabric layer, first nonwoven fabric layer/melt-blown nonwoven fabric layer/second nonwoven fabric layer/first nonwoven fabric layer, first nonwoven fabric layer/first nonwoven fabric layer/melt-blown nonwoven fabric layer/second nonwoven fabric layer/second nonwoven fabric layer, first nonwoven fabric layer/first nonwoven fabric layer/melt-blown nonwoven fabric layer/second nonwoven fabric layer/melt-blown nonwoven fabric layer, first nonwoven fabric layer/melt-blown nonwoven fabric layer/first nonwoven fabric layer/second nonwoven fabric layer, first nonwoven fabric layer/melt-blown nonwoven fabric layer/first nonwoven fabric layer/second nonwoven fabric layer/first nonwoven fabric layer, first nonwoven fabric layer/melt-blown nonwoven fabric layer/first nonwoven fabric layer/second nonwoven fabric layer/second nonwoven fabric layer, first nonwoven fabric layer/first nonwoven fabric layer/second nonwoven fabric layer/melt-blown nonwoven fabric layer/first nonwoven fabric layer/first nonwoven fabric layer, first nonwoven fabric layer/second nonwoven fabric layer/melt-blown nonwoven fabric layer/first nonwoven fabric layer/second nonwoven fabric layer, first nonwoven fabric layer/second nonwoven fabric layer/melt-blown nonwoven fabric layer/first nonwoven fabric layer/melt-blown nonwoven fabric layer, first nonwoven fabric layer/melt-blown nonwoven fabric layer/second nonwoven fabric layer/first nonwoven fabric layer, first nonwoven fabric layer/second nonwoven fabric layer/melt-blown nonwoven fabric layer/first nonwoven fabric layer, first nonwoven fabric layer/melt-blown nonwoven fabric layer/second nonwoven fabric layer/second nonwoven fabric layer/second nonwoven fabric layer, first nonwoven fabric layer/second nonwoven fabric layer/melt-blown nonwoven fabric layer/second nonwoven fabric layer/first nonwoven fabric layer, first nonwoven fabric layer/melt-blown nonwoven fabric layer/second nonwoven fabric layer/second nonwoven fabric layer/second nonwoven fabric layer, first nonwoven fabric layer/melt-blown nonwoven fabric layer/second nonwoven fabric layer/melt-blown nonwoven fabric layer, first nonwoven fabric layer/second nonwoven fabric layer/melt-blown nonwoven fabric layer/second nonwoven fabric layer/second nonwoven fabric layer, first nonwoven fabric layer/melt-blown nonwoven fabric layer/second nonwoven fabric layer/second nonwoven fabric layer/second nonwoven fabric layer, first nonwoven fabric layer/melt-blown nonwoven fabric layer/second nonwoven fabric layer/melt-blown nonwoven fabric layer/second nonwoven fabric layer, first nonwoven fabric layer/first nonwoven fabric layer/melt-blown nonwoven fabric layer/melt-blown nonwoven fabric layer/first nonwoven fabric layer, first nonwoven fabric layer/melt-blown nonwoven fabric layer/melt-blown nonwoven fabric layer/second nonwoven fabric layer/first nonwoven fabric layer, and first nonwoven fabric layer/melt-blown nonwoven fabric layer/melt-blown nonwoven fabric layer/second nonwoven fabric layer/second nonwoven fabric layer.

Since the nonwoven fabric layered body includes the melt-blown nonwoven fabric layer, breathability is reduced and a barrier property (particle trapping property) is improved. Therefore, the nonwoven fabric layered body can be suitably used for filters, wrapping fine particles (packaging materials for absorbent bodies of diapers, or pet sheets), and the like.

On the other hand, the nonwoven fabric layered body including the melt-blown nonwoven fabric layer tends to have worse flexibility, especially a cantilever value, than the nonwoven fabric layered body not including the melt-blown nonwoven fabric layer. By combining the first nonwoven fabric layer, the second nonwoven fabric layer, and the melt-blown nonwoven fabric layer, the aforementioned deterioration of flexibility can be suitably suppressed, and further, for example, by setting the basis weight, the average fiber diameter of the fibers or the like of the melt-blown nonwoven fabric layer to the aforementioned range, or by using the aforementioned thermoplastic polymer, the aforementioned deterioration of flexibility can be more suitably suppressed.

The fibers made of the thermoplastic polymer included in the first made fabric layer, the second nonwoven fabric layer and the melt-blown nonwoven fabric layer may include commonly used additive, if necessary. Examples of the additive include various known additives such as an antioxidant, weather-resistant stabilizer, a heat-resistant stabilizer, a light-resistant stabilizer, an antistatic agent, an anti-fogging agent, a lubricant, a dye, a pigment, a natural oil, a synthetic oil, and a wax.

The nonwoven fabric layered body in the present disclosure includes a hydrophilic agent. The hydrophilic agent can be further classified into a penetrant and a humectant. The nonwoven fabric layered body in the present disclosure may include both the penetrant and the humectant, or may not include the penetrant and may include the humectant. From the viewpoint of being excellent in hydrophilicity and further exhibiting the migration suppressing effect of the hydrophilic agent, it is preferable to include both the penetrant and the humectant as the hydrophilic agent.

The hydrophilic agent preferably includes at least one of a sulfonate or a sulfate ester salt as the penetrant. Examples of the sulfonate include an alkylbenzene sulfonate, an alkylnaphthalene sulfonate, an α-olefin sulfonate, and an alkylsulfosuccinate. These sulfonates are preferably alkali metal salts. Examples of the sulfate ester salt include a higher alcohol sulfate ester salt and an alkyl sulfate ester salt. These sulfate ester salts are preferably alkali metal salts. Among these, the hydrophilic agent preferably includes the sulfonate and more preferably includes an alkali metal salt of a sulfonic acid as the penetrant.

From the viewpoint of suppressing the migration of the hydrophilic agent when it comes into contact with another member, the sulfonate as the penetrant is preferably the alkyl sulfosuccinate. The alkyl sulfosuccinate is preferably an alkali metal salt of a dialkylsulfosuccinic acid, and more preferably an alkali metal salt of a dialkylsulfosuccinic acid with two alkyl groups having 8 to 16 carbon atoms. Examples of the alkali metal salt of a dialkylsulfosuccinic acid include a lithium salt thereof, a sodium salt thereof, and a potassium salt thereof, and the sodium salt thereof is preferable. Examples of the alkali metal salt of a dialkylsulfosuccinic acid with two alkyl groups having 8 to 16 carbon atoms, include a sodium dioctyl sulfosuccinate, a sodium di(2-ethylhexyl) sulfosuccinate, a sodium didecyl sulfosuccinate, a sodium didodecyl sulfosuccinate, a lithium (Li) ditetradecyl sulfosuccinate, and a potassium (K) dihexadecyl sulfosuccinate. Among these, the sodium di(2-ethylhexyl) sulfosuccinate is preferable from the viewpoint of suppressing the migration of the hydrophilic agent when it comes into contact with another member.

The hydrophilic agent may include any of a cationic surfactant, an anionic surfactant, an amphoteric surfactant, and a nonionic surfactant as the humectant, and the humectant is not particularly limited.

Examples of the cationic surfactant include alkyl (or alkenyl) trimethylammonium halides, quaternary ammonium salts typified by dialkyl (or alkenyl) dimethylammonium halides, and alkylamine salts, and alkylene oxide adducts thereof. Examples of the anionic surfactant include phosphate ester salts typified by sodium lauryl phosphate and fatty acid salts typified by sodium laurate. Examples of the amphoteric surfactant include salts of these cationic surfactants and anionic surfactants.

From the viewpoint of imparting excellent hydrophilicity, the humectant is preferably the nonionic surfactant. Examples of the nonionic surfactant that is the humectant include polyhydric alcohol fatty acid esters, polyoxyalkylene fatty acid esters, alkylpolyoxyethylene alcohols, alkylene oxide adducts of polyhydric alcohol fatty acid esters, alkoxylated alkylphenols, fatty acid amides, alkyldiethanolamides and polyoxyalkylenes. Among these, from the viewpoint of imparting excellent hydrophilicity, the hydrophilic agent preferably includes, as the humectant, at least one selected from the group consisting of polyhydric alcohol fatty acid esters, polyoxyalkylene fatty acid esters, and alkylene oxide adducts of polyhydric alcohol fatty acid esters. Polyhydric alcohol fatty acid esters, polyoxyalkylene fatty acid esters, and alkylene oxide adducts of polyhydric alcohol fatty acid esters may be any of monoester, diester, and triester, respectively. Polyhydric alcohol fatty acid esters, polyoxyalkylene fatty acid esters, and alkylene oxide adducts of polyhydric alcohol fatty acid esters, respectively, may individually include one selected from a monoester, a diester, and a triester, or may include two or more selected from a monoester, a diester, and a triester.

Examples of the polyhydric alcohol fatty acid esters include glycerin fatty acid esters, and sorbitan fatty acid esters. Both the glycerin fatty acid esters and the sorbitan fatty acid esters are preferably esters of glycerin or sorbitan and a fatty acid having 10 to 20 carbon atoms. Specific examples thereof include glycerin lauric acid monoesters, glycerin oleic acid diesters, glycerin oleic acid triesters, sorbitan lauric acid monoesters, sorbitan lauric acid diesters, and sorbitan lauric acid triesters.

Examples of the polyoxyalkylene fatty acid esters include polyoxyethylene fatty acid esters, and polyoxypropylene fatty acid esters. Among these, polyoxyethylene fatty acid esters are preferable. In the polyoxyethylene fatty acid esters, it is preferable that the fatty acid has 10 to 20 carbon atoms, and additional moles of the ethylene oxide chain (also referred to as EO chain) are from 5 to 20. Specific examples thereof include polyoxyethylene stearic acid monoesters, polyoxyethylene lauric acid monoesters, polyoxyethylene lauric acid diesters, polyoxyethylene oleic acid monoesters, and polyoxyethylene oleic acid diesters.

Examples of the alkylene oxide adducts of polyhydric alcohol fatty acid esters include ethylene oxide adducts of polyhydric alcohol fatty acid esters and propylene oxide adducts of polyhydric alcohol fatty acid esters. Among these, it is preferable that the alkylene oxide adducts of polyhydric alcohol fatty acid esters are esters of glycerin and a fatty acid having 10 to 20 carbon atoms, and additional moles of ethylene oxide are from 5 to 20. Specific examples thereof include polyoxyethylene glycerin lauric acid monoesters, polyoxyethylene glycerin lauric acid diesters, and polyoxyethylene glycerin lauric acid triesters.

From the viewpoint of imparting excellent hydrophilicity, the humectant is preferably included in combination with the polyhydric alcohol fatty acid ester, the alkylene oxide adduct of a polyhydric alcohol fatty acid ester, and the polyoxyalkylene fatty acid ester. The humectant is also preferably included in combination with the polyhydric alcohol fatty acid ester and the polyoxyalkylene fatty acid ester.

The combination of the polyhydric alcohol fatty acid ester, the alkylene oxide adduct of a polyhydric alcohol fatty acid ester, and the polyoxyalkylene fatty acid ester is more preferably a combination of the glycerin fatty acid ester, the ethylene oxide adduct of a polyhydric alcohol fatty acid ester, and a polyoxyethylene fatty acid ester. A combination of a glycerin oleic acid diester, a polyoxyethylene glycerin lauric acid diester and triester, and a polyoxyethylene lauric acid diester is further preferable.

A combination of the polyhydric alcohol fatty acid ester and the alkylene oxide adduct of a polyhydric alcohol fatty acid ester is preferably a combination of the glycerin fatty acid ester and the alkylene oxide adduct of a polyhydric alcohol fatty acid ester, and more preferably a combination of a glycerin oleic acid diester and a glycerin oleic acid triester and a polyoxyethylene oleic acid monoester and a polyoxyethylene oleic acid diester.

The combination of the polyhydric alcohol fatty acid ester and the polyoxyalkylene fatty acid ester is preferably a combination of a sorbitan lauric acid monoester, diester and triester, and, a polyoxyethylene lauric acid monoester and diester, or it is also preferable to combine a polyoxyethylene sorbitan oleic acid monoester, a polyoxyethylene sorbitan oleic acid diester and a polyoxyethylene sorbitan oleic acid triester in addition to these sorbitan lauric acid esters and polyoxyethylene lauric acid esters.

A mass ratio (penetrant/humectant) of the penetrant with respect to the humectant, is preferably from 1/99 to 60/40, more preferably from 5/95 to 50/50, and further preferably from 10/90 to 40/60. In a case in which the mass ratio of penetrant/humectant is in this range, it tends to have excellent hydrophilicity and the migration of the hydrophilic agent when it comes into contact with another member tends to be suppressed.

When 0.02 g of the above hydrophilic agent is added to 20 ml of 1/1 (mass ratio) mixed solution of hexane/water and the mixed solution is stirred after the hydrophilic agent is added, it is preferable to separate an oil phase and an aqueous phase after 1 minute (hereinafter, also referred to as a separation test of the hydrophilic agent). This separation test is considered to be an indicator of the affinity of the hydrophilic agent as a whole for water or the fibers made of the thermoplastic polymer. In a case in which the hydrophilic agent separates into the oil phase and the aqueous phase, it is considered to have a higher affinity for water, and in a case in which the hydrophilic agent does not separate, it is considered to have a higher affinity for the fibers made of the thermoplastic polymer. Therefore, by using the hydrophilic agent separating by the above separation test, hydrophilicity tends to be further improved. In the hydrophilic agent exhibiting such properties, the mass ratio of penetrant/humectant is preferably from 1/99 to 60/40, and more preferably from 10/90 to 40/60.

For example, when analyzing the hydrophilic agent from the nonwoven fabric to be measured, the separation test of the hydrophilic agent may be measured as follows. First, a nonwoven fabric of 100 g or more is prepared. Next, the prepared nonwoven fabric is immersed in ethanol and allowed to stand at 25° C. for 24 hours to obtain an extract A. The nonwoven fabric is immersed in another ethanol and allowed to stand at 25° C. for 24 hours to obtain an extract B. The extract A and the extract B are degassed and heated to 80° C. to sufficiently remove ethanol and to obtain a residue. Then, the residue is mixed and the residue is subjected to the separation test of the hydrophilic agent.

A coating amount of the hydrophilic agent is preferably from 0.1% by mass to 2.0% by mass, more preferably from 0.2% by mass to 1.5% by mass, and further preferably from 0.3% by mass to 1.2% by mass. In a case in which the coating amount of the hydrophilic agent is in this range, it tends to have excellent hydrophilicity and the migration of the hydrophilic agent when it comes into contact with another member tends to be suppressed. The coating amount of the hydrophilic agent is represented as a percentage obtained by subtracting the mass of the nonwoven fabric before applying the hydrophilic agent from the mass of the nonwoven fabric after applying the hydrophilic agent, and dividing the value by the mass of the nonwoven fabric before applying the hydrophilic agent. In the present disclosure, the coating amount of the hydrophilic agent is a concept that is included as the coating amount even in the case of the kneading method.

The nonwoven fabric layered body in the present disclosure may include another component, if necessary. Examples of another component include various known additives such as an antioxidants, a heat-resistant stabilizer, a weather-resistant stabilizer, an antistatic agent, a slip agent, an antifogging agent, a lubricant, a dye, a pigment, a light-resistant stabilizer, an anti-blocking agent, a dispersant, a nucleating agent, a fabric softener, a water repellent, a filler, a natural oil, a synthetic oil, a wax, an antibacterial agent, a preservative, a matting agent, a rust preventive, a fragrance, a defoamer, a fungicide, and an insect repellent. These other components may be included inside the fiber constituting the nonwoven fabric, or may be attached to the surface of the fiber.

In the nonwoven fabric layered body in the present disclosure, a transfer amount (hereinafter, also referred to as the transfer amount) of the hydrophilic agent from the nonwoven fabric layered body to a nonwoven fabric transfer target is preferably 0.015 $g/m^2$ or less, more preferably 0.013 $g/m^2$ or less, and further preferably 0.011 $g/m^2$ or less. In a case in which the transfer amount is in the above range, the nonwoven fabric layered body is excellent in hydrophilicity and the migration of the hydrophilic agent when it comes into contact with another member is suppressed. The measurement method of the transfer amount is explained in Examples described later. For example, the above range of the transfer amount can be satisfied by adjusting the production conditions such as the type, the amount and the coating method of the hydrophilic agent included in the nonwoven fabric layered body. In the nonwoven fabric layered body in the present disclosure, the transfer amount of the hydrophilic agent from the nonwoven fabric layered body to a nonwoven fabric transfer target is not particularly limited as long as the transfer amount is 0 g/m² or more, and for example, may be 0.001 g/m² or more.

In the nonwoven fabric layered body in the present disclosure, a ratio (surface water vapor adsorption area/surface nitrogen adsorption area, hereinafter, also referred to as the area ratio) of a surface water vapor adsorption area obtained by a BET formula of a water vapor adsorption isotherm in a water vapor adsorption test with respect to a surface nitrogen adsorption area obtained by a BET formula of a nitrogen adsorption isotherm in a nitrogen adsorption test is preferably 1.5 or more, more preferably 3.0 or more, and further preferably 5.0 or more. The area ratio is preferably 9.0 or less, and more preferably 8.5 or less. The area ratio is an indicator of the balance between hydrophilicity and hydrophobicity per surface area of the nonwoven fabric. In a case in which the area ratio is in the above range, the nonwoven fabric is excellent in hydrophilicity and the migration of the hydrophilic agent when it comes into contact with another member is suppressed. The measurement method of a surface water vapor adsorption area obtained by a BET formula of a water vapor adsorption isotherm in a water vapor adsorption test and the measurement method of a surface nitrogen adsorption area obtained by a BET formula of a nitrogen adsorption isotherm in a nitrogen adsorption test are explained in Examples described later. For example, the above range of the ratio of the surface water vapor adsorption area with respect to the surface nitrogen adsorption area can be satisfied by adjusting the production conditions such as the type, the amount and the coating method of the hydrophilic agent included in the nonwoven fabric layered body.

In the nonwoven fabric layered body in the present disclosure, a width retention rate is preferably 75% or more, and more preferably 77% or more, in a case in which a tensile stress of 0.1 N/mm is applied in an MD direction of the nonwoven fabric layered body. When the width retention rate is 75% or more in a case in which a tensile stress of 0.1 N/mm is applied, dimensional stability is excellent.

In the nonwoven fabric layered body in the present disclosure, a tensile strength at the time of 5% stretching in an MD direction of the nonwoven fabric layered body is preferably 2.2 N/50 mm or more and more preferably 2.5 N/50 mm or more.

From the viewpoint of excellent flexibility, the nonwoven fabric layered body in the present disclosure may include a pressure bonding portion and a non-pressure bonding portion. A area rate of the pressure bonding portion is preferably from 7% to 20% and more preferably from 8% to 18%. The area rate of the pressure bonding portion is set at the rate of the area of a thermocompression bonding portion with respect to the area of an observed test piece, in a case in which the test piece having a size of 10 mm×10 mm is sampled from the nonwoven fabric layered body, and a surface of the test piece, which has come into contact with the embossing roll, is observed with an electron microscope (magnification: 100 times).

From the viewpoint of flexibility, the nonwoven fabric layered body in the present disclosure preferably has the following characteristics.

A compression work WC measured by the KES method is preferably 0.15 or more. The difference (TO−TM) between a thickness TO at a pressure of 0.5 gf/cm² measured by the KES method in compression characteristics test and a thickness TM at a pressure of 50 gf/cm² measured by the KES method is preferably 0.2 or more.

The KES (Kawabata Evaluation System) method is one of the methods for measuring the texture of nonwoven fabric and objectively evaluating it.

The compression work WC, the thickness TO at a pressure of 0.5 gf/cm², and the thickness TM at a pressure of 50 gf/cm² are measured with a testing machine KES-FB3-A manufactured by Kato Tech Co., Ltd. Specifically, measurement are performed while compressing a sample from 0 gf/cm² to a maximum pressure of 50 gf/cm² at a compression deformation rate of 0.020 mm/sec between steel pressure plates having a circular plane with a compression area of 2 cm² and returning it to its original state.

The compression work WC means a compression work in the compression test by the KES method. From the viewpoint of excellent flexibility of the nonwoven fabric layered body, the compression work WC is preferably 0.15 gf·cm/cm² or more, and more preferably 0.17 gf·cm/cm² or more. The upper limit of the compression work WC is not particularly limited, and for example, is preferably 1.00 gf·cm/cm² or less.

The thickness TO at a pressure of 0.5 gf/cm² is a thickness at a pressure of 0.5 gf/cm² in the compression test by the KES method, and represents the initial thickness. TO is preferably 0.40 mm or more, and more preferably 0.50 mm or more.

The thickness TM at a pressure of 50 gf/cm² is a thickness at a pressure of 0.5 gf/cm² in the compression test by the KES method, and represents the thickness at maximum compression. TM is preferably 0.10 mm or more, and more preferably 0.15 mm or more.

TO−TM is a difference between the above TO and the above TM. The larger TO−TM is, the better the bulkiness is. TO−TM is preferably 0.20 mm or more, and more preferably 0.25 mm or more. The upper limit of TO−TM is not particularly limited, and for example is preferably 1.00 mm or less.

In the nonwoven fabric layered body in the present disclosure, an air permeability measured under the condition of a flow rate with a pressure difference of 125 Pa by a Frazier air permeability measuring machine according to JIS L 1096: 2010 is preferably 500 cm³/cm²/sec or less, more preferably 400 cm³/cm²/sec or less, and further preferably 300 cm³/cm²/sec or less. The lower limit of the air permeability is not particularly limited, and may be 20 cm³/cm²/sec or more, or may be 50 cm³/cm²/sec or more.

In a case in which the air permeability of the nonwoven fabric layered body is in the above range, appropriate breathability and barrier property can be obtained. The obtained nonwoven fabric layered body is excellent in strength. In a case in which the nonwoven fabric layered body in the present disclosure includes the melt-blown layer, the air permeability in the above range is easily obtained.

A manufacturing method of the nonwoven fabric layered body in the present disclosure is not particularly limited.

Examples of a method to include the hydrophilic agent in the nonwoven fabric layered body include the following method.

(1): A method of imparting hydrophilicity to a nonwoven fabric by forming the nonwoven fabric with the fiber made of the thermoplastic polymer kneaded with the hydrophilic agent (kneading method).

(2): A method of imparting hydrophilicity to a nonwoven fabric by adhering the hydrophilic agent to the fiber surface (coating method).

Examples of the manufacturing method of the nonwoven fabric layered body in the present disclosure include the following method.

Method 1 (kneading method): a method including a step of mixing the hydrophilic agent with a raw material of the thermoplastic polymer, and a step of forming the nonwoven fabric layered body including the fiber, made of the thermoplastic polymer, including the hydrophilic agent.

Method 2 (coating method): a method including a step of forming a nonwoven fabric including the fiber made of the thermoplastic polymer and a step of adhering the hydrophilic agent to the nonwoven fabric.

For example, the step of forming a nonwoven fabric may form the nonwoven fabric layered body by a known method for manufacturing a long fiber nonwoven fabric and a known method for manufacturing a short fiber nonwoven fabric. In a case in which the nonwoven fabric layered body is the first nonwoven fabric layer constituted by a spunbond nonwoven fabric and the second nonwoven fabric layer constituted by a spunbond nonwoven fabric, one example of the manufacturing method of the nonwoven fabric layered body in the present disclosure preferably has the following steps.

A step of melt-spinning a first thermoplastic polymer to form a first continuous fiber (first spinning step).

A step of depositing the first continuous fiber on a movable collecting member to form the first nonwoven web (nonwoven web forming step).

A step of melt-spinning a second thermoplastic polymer to form a second continuous fiber (second spinning process)

A step of depositing the second continuous fiber on the first nonwoven web to form a second nonwoven web and to form a layered nonwoven web (layered nonwoven web forming step).

A step of entangling the layered web (entangling step)

Method 1 has a step of mixing the hydrophilic agent with at least one of the first thermoplastic polymer and the second thermoplastic polymer. Examples of this step include mixing the hydrophilic agent with at least one spinning dope of the first thermoplastic polymer and the second thermoplastic polymer.

The first spinning step includes a known process of cooling the first continuous fiber to stretch it before depositing it on the movable collecting member. The second spinning step also includes a known process of cooling the second continuous fiber to stretch it before depositing it on the first nonwoven web.

The entangling step is not particularly limited and examples thereof include a known entanglement process. From the viewpoint of exhibiting both excellent flexibility and strength (line suitability), the entanglement process is preferably thermocompression bonding with an embossed roll is preferred. It is preferable to apply the embossed roll with an area ratio of a convex portion of from 7% to 20%.

Method 2 has a step of adhering the hydrophilic agent to the nonwoven fabric layered body after an entanglement process. If necessary, a squeezing step and a drying step may be provided. As long as the hydrophilic agent can be attached to the nonwoven fabric, the method of adhering the hydrophilic agent is not particularly limited. For example, the hydrophilic agent is preferably attached by applying a solution in which the hydrophilic agent is dissolved in a solvent (for example, a volatile organic solvent such as methanol, ethanol, isopropyl alcohol, or water) to a nonwoven fabric. Examples of the method for adhering the hydrophilic agent to the nonwoven fabric include known methods such as dipping (immersion), roll coating (gravure coating, kiss coating), spray coating, and die coating. In the present disclosure, "coating" is a concept that includes "dipping (immersion)".

In adhering the hydrophilic agent to the nonwoven fabric layered body, it is preferable to dissolve the hydrophilic agent in a solvent such as water to obtain a solution of the hydrophilic agent, and to apply the solution of the hydrophilic agent to the nonwoven fabric. From the viewpoint of facilitating the application of the solution of the hydrophilic agent, it is preferable that the solution of the hydrophilic agent includes the penetrant and the humectant as active ingredients, and the total amount of the active ingredients is from 0.10% by mass to 30% by mass. The solution of the hydrophilic agent may include additives such as an antibacterial agent, an antioxidant, a preservative, a matting agent, a pigment, a rust preventive, a fragrance and a defoamer, depending on the purpose.

In the manufacturing method of the nonwoven fabric layered body in the present disclosure, for example, melt-spinning may be performed by a melt-blown method, a fiber may be deposited on the first nonwoven web to form a melt-blown web, and a second continuous fiber may be deposited on the melt-blown web to form a second nonwoven web and to form a layered nonwoven web. In the aforementioned method 1, the hydrophilic agent may be mixed with the thermoplastic polymer constituting the melt-blown nonwoven fabric layer.

<Composite Layered Body>

A composite layered body in the present disclosure includes the nonwoven fabric layered body in the present disclosure. The composite layered body may be a composite structure in which the nonwoven fabric layered body in the present disclosure and another layer other than the nonwoven fabric layered body in the present disclosure are layered. Another layer may be one layer, or may be two or more layers. In the present disclosure, a layered body provided with another layer other than the nonwoven fabric layered body in the present disclosure is referred to as "composite layered body".

Examples of another layer include fiber aggregates such as a knitted fabric, a woven fabric, and a nonwoven fabric (short fiber nonwoven fabric, long fiber nonwoven fabric) other than the nonwoven fabric layered body in the present disclosure. Examples of the nonwoven fabric other than the nonwoven fabric layered body in the present disclosure include various known nonwoven fabrics (spunbond nonwoven fabric, melt-blown nonwoven fabric, wet nonwoven fabric, dry nonwoven fabric, dry pulp nonwoven fabric, flashspun nonwoven fabric, spread nonwoven fabric, and the like). The fiber aggregate may be a sheet of natural fibers such as cotton. The term "long fiber" refers to "continuous filament" generally used in the art, such as the Nonwoven Fabric Handbook (edited by INDA Association of the Nonwoven Fabrics Industry, Nonwoven Fabric Report Co., Ltd., 1996).

Examples of another layer include resin films such as polyolefin, polyester, and polyamide. These may be layered in combination. For example, the nonwoven fabric layered body in the present disclosure, a resin film, and a fiber aggregate of natural fibers such as cotton may be layered in this order.

As the film to be layered with the nonwoven fabric layered body in the present disclosure, a breathable film or a moisture-permeable film is preferable in a case in which the layered body requires breathability.

Examples of the breathable film include various known breathable films. Examples thereof include a film of thermoplastic elastomers such as a moisture-permeable polyurethane elastomer, a polyester elastomer, and a polyamide elastomer, and a porous film obtained by stretching a thermoplastic resin film including inorganic particles or organic particles to make it porous. Examples of the thermoplastic resin used for the porous film include polyolefins such as a high pressure low density polyethylene, a linear low density polyethylene (so-called LLDPE), a high density polyethylene, polypropylene, a polypropylene random copolymer, and a combination thereof.

In a case in which the nonwoven fabric layered body does not require breathability, one or more non-porous thermoplastic resin films selected from polyolefins (polyethylene, polypropylene, and the like), polyesters, and polyamides may be used.

A method of further layering (laminating) another layer to the nonwoven fabric layered body in the present disclosure is not particularly limited, and example thereof include various methods such as thermal fusion methods such as thermal embossing, and ultrasonic fusion, mechanical entanglement methods such as needle punching and water-jets, methods using adhesives such as hot melt adhesives and urethane adhesives, and extrusion lamination.

<Cover Sheet>

A cover sheet in the present disclosure includes the nonwoven fabric layered body in the present disclosure. The cover sheet in the present disclosure is not particularly limited as long as the cover sheet includes the nonwoven fabric layered body or the composite layered body in the present disclosure. The cover sheet in the present disclosure refers to a sheet for covering at least a part of a target object. The cover sheet is not particularly limited, and has various uses. Specifically, Examples of uses to which the cover sheet is applied include absorbent articles (disposable napkins, disposable pants, sanitary napkins, urine absorbing pads, top sheets such as pet sheets, second sheets, and packaging material (core wrap) for absorbers (pulp/polymer absorbent particles); cosmetic materials (face masks, and the like); sanitary materials (wet cloth materials, sheets, towels, industrial masks, sanitary masks, hair caps, gauze, disposable underwear, and the like); and packaging materials (deoxidizers, hot packs, warm poultices, food packaging materials). Furthermore, it can be applied to general living materials such as clothes covers. It can also be suitably used as automobile interior materials and various backing materials. It can be widely applied as filter materials such as liquid filters and air filters.

EXAMPLES

The nonwoven fabric body in the present disclosure will be explained with reference to Examples. However, the nonwoven fabric body in the present disclosure is not limited to the following embodiments.

In the following Examples, "%" represents "% by mass".

Physical property values and the like in Examples and Comparative Examples were measured by the following methods.

(1) Basis Weight [g/m$^2$]

Ten test pieces of 100 mm (machine direction: MD)×100 mm (direction orthogonal to machine direction: CD) were collected from an obtained nonwoven fabric layered body. Places at which the test pieces were collected were set at ten places in the CD direction. Then, the mass [g] of each collected test piece was measured using an electronic balance scale (manufactured by Kensei Co., LTD.). The average value of the masses of the test pieces was determined. The determined average value was converted into a mass [g] per 1 m$^2$, which was rounded off to one decimal place to obtain a value, which was regarded as the basis weight [g/m$^2$] of each nonwoven fabric sample.

(2) Thickness [mm]

Ten test pieces of 100 mm (MD)×100 mm (CD) were collected from the obtained nonwoven fabric layered body. Places at which the test pieces were collected were set at places similar to the test pieces for measuring the basis weight. Then, the thickness [mm] of each collected test piece was measured by a method described in JIS L 1096: 2010, using a load-type thickness gauge (manufactured by OZAKI MFG. CO., LTD.). The average value of the thicknesses of the test pieces was determined, and rounded off to one decimal place to obtain a value, which was regarded as the thickness [mm] of each nonwoven fabric sample.

[Evaluation of Flexibility]

(3) WC Value (Compression Work)[gf·cm/cm$^2$]

Two test pieces of 150 mm (MD)×150 mm (CD) were collected from an obtained nonwoven fabric layered body. Places at which the test pieces were collected were set at two places in the CD direction. Then, the compression test was performed to the test pieces with a testing machine KES-FB3-A manufactured by Kato Tech Co., Ltd under the condition of RH environment of 20° C. and 50% relative humidity, using compressors (steel pressure plates having a circular plane with a compression area of 2 cm$^2$) and at a compression deformation rate of 0.020 mm/sec and a maximum pressure of 50 gf/cm$^2$, and rounded off to two decimal place to obtain a value, which was regarded as WC Value [gf·cm/cm$^2$] of each nonwoven fabric sample.

[Evaluation of Bulkiness]

(4) TO (Thickness TO at Pressure of 0.5 gf/cm$^2$)–TM (Thickness TO at Pressure of 50 gf/cm$^2$)[mm]

Two test pieces of 150 mm (MD)×150 mm (CD) were collected from an obtained nonwoven fabric layered body. Places at which the test pieces were collected were set at two places in the CD direction. Then, the compression test was performed to the test pieces with a testing machine KES-FB3-A manufactured by Kato Tech Co., Ltd under the condition of RH environment of 20° C. and 50% relative humidity, using compressors (steel pressure plates having a circular plane with a compression area of 2 cm$^2$) and at a compression deformation rate of 0.020 mm/sec and a maximum pressure of 50 gf/cm$^2$, to measure TO [mm] and TM [mm].

The average values of TO [mm] and TM [mm] of test samples were determined, and rounded off to two decimal place to obtain values which were regarded as TO [mm] and TM [mm] of each nonwoven fabric sample. TO–TM [mm] of each nonwoven fabric sample was calculated.

(5) Cantilever Method

In an obtained nonwoven fabric layer body, a bending resistance was measured in each of the MD direction and the CD direction in accordance with the cantilever method (ISO method) of JIS L 1913: 2010.

[Evaluation of Strength]

(6) Tensile Strength, and Strength at the Time of 5% Stretching [N/50 mm]

The obtained nonwoven fabric layered body was measured in accordance with JIS L 1906. A test piece having 50 mm in width×200 mm in length was collected from the nonwoven fabric, MD: five points were measured at a distance between chucks of 100 mm and a head speed of 100 mm/min using a tensile tester, an average value was calculated, and the tensile strength (N/50 mm) was determined. In the measurement program, the strength recorded at the time of 5% stretching (between chucks: 105 mm) was defined as the strength at the time of 5% stretching.

[Evaluation of Dimensional Stability]
(7) Width Retention Rate [%]

For the obtained nonwoven fabric layered body, a test piece having 200 mm in width×450 mm in length (or 100 mm in width×450 mm in length if it cannot be collected) was collected and both ends in the width direction were sandwiched by tools that can be pulled in a nearly uniform state. The distance between the tools is 350 mm. Set it on a tensile tester, pull it with a tension of 0.1 N/mm, and measure the width at that time. Then, the width retention rate (%) is determined by the following formula.

Width Retention Rate(%) =
{Width when pulled (mm)/Initial Width (mm)} × 100

(8) Drying Furnace Suitability

In a case in which the width retention rate was less than 75%, it was judged that drying furnace suitability was poor (indicated as "B" in the table). In a case in which the width retention rate was 75% or more, it was judged that drying furnace suitability was good (indicated as "A" in the table).

[Evaluation of Hydrophilicity]
(9) Liquid Flow Distance [mm]

The obtained nonwoven fabric layered body was cut into a size of 100 mm×200 mm to be used as a sample. Five filter papers (No. 2, manufactured by Advantech) were placed on a plate fixed at an angle of 45 degrees with respect to the horizontal direction, and the sample was placed on the filter paper, and both ends in the longitudinal direction of the sample was fixed together with the filter paper on the board. In an environment of 25° C., from a height of about 10 mm in the direction perpendicular to the sample surface, dropped 0.1 ml of artificial urine with a dropper, and a distance from the drop point of the droplet to the point where the droplet was completely absorbed was measured and the measured value was regarded as the liquid flow distance (mm).

The liquid flow distance was evaluated based on the following evaluation criteria. The results are shown in Table 1.

For the artificial urine, an aqueous solution of sodium chloride (9 g/liter) having a surface tension of 70±2 mN/m was used.

(10) Strike-Through Test

It was measured according to EDANA (European Disposables And Nonwovens Association) standard NWSP 070.8. RO (15). The first result and the third result were recorded.

[Migration Evaluation of Hydrophilizing Agent]
(11) Migration Evaluation

The nonwoven fabric layered body obtained in each example was cut into a size of 100 mm×100 mm. A nonwoven fabric (nonwoven fabric transfer target) composed of homopolypropylene with a basis weight of 25 g/m$^2$ and not including the hydrophilic agent was cut into a size of 100 mm×100 mm. The two nonwoven fabrics were put together, and a 4 kg weight with a cross-sectional area of 100 mm×100 mm was placed on the two nonwoven fabrics. In order to prevent the transfer of the hydrophilic agent to the weight and the floor surface, they may be wrapped with a film. The nonwoven fabrics on which the weight was placed was left in an environment of 60° C. and a relative humidity of 80% for 1 week. The nonwoven fabric transfer target was taken out, 0.2 ml of water was added dropwise, and the infiltration of water was evaluated.

When it was infiltrated, it was judged that hydrophilicity was strongly expressed, and the migration of the hydrophilic agent was bad (indicated as "C" in the table). When it was infiltrated but the expression of hydrophilicity was weak, it was judged that the migration of the hydrophilic agent was bad (indicated as "B" in the table). When it was not infiltrated, it was judged that hydrophilicity was not expressed, and the migration of the hydrophilic agent was good (indicated as "A" in the table).

(12) Transfer Amount of Hydrophilizing Agent from Nonwoven Fabric Layered Body to Nonwoven Fabric Transfer Target The nonwoven fabric transfer target prepared as described above was extracted with methanol using a rapid residual fat extractor OC-1 type (manufactured by INTEC CO., LTD.), the solvent was completely distilled off from the extract, and the mass of the transferred hydrophilic agent was determined. Then, from the following formula, the hydrophilic agent adhesion rate C % and the hydrophilic agent amount W3 (g/m$^2$) transferred from the nonwoven fabric layered body to the nonwoven fabric transfer target were determined. Since the optimum weight of the nonwoven fabric for this measurement is about 2 g, eight to ten sheets of the above nonwoven fabric transfer target were prepared and measured.

$$C(\%) = (W2/W1) \times 100$$

W1: Nonwoven fabric mass (g) of nonwoven fabric transfer target

W2: Mass (g) of hydrophilic agent (=transferred hydrophilic agent) in the extract W3 (g/m$^2$): Transfer amount of hydrophilic agent from nonwoven fabric layered body to nonwoven fabric transfer target (C (%)×25 (g/m$^2$)×100)

(13) Ratio of Surface Water Vapor Adsorption Area with Respect to Surface Nitrogen Adsorption Area The measurement was performed using BELSORP-max, a device manufactured by Microtrack Bell Co., Ltd.

Specifically, it was done as follows. First, a sample of about 0.50 g to 1.0 g was taken from the nonwoven fabric and set it in the device. Next, a drying processing by vacuum exhaust was performed at room temperature (25° C.) for 8 hours. Then, water vapor was adsorbed at 25° C. by changing the introduction pressure, and the water vapor adsorption isotherm was measured by plotting the water vapor adsorption amount for each introduction pressure. Then, the following BET formula was applied to determine the specific surface area [m$^2$/g] as the surface water vapor adsorption area.

Next, the sample collection to the test were performed in the same procedure as the water vapor adsorption test except that nitrogen was used instead of water vapor, and the nitrogen adsorption isotherm was measured. Then, the specific surface area as the surface nitrogen adsorption area was determined by the following BET formula. From the specific surface area as the surface water vapor adsorption area obtained above and the specific surface area as the surface nitrogen adsorption area obtained above, the ratio was calculated by "(specific surface area with water vapor)÷(specific surface area with nitrogen)".

The BET formula is an equation expressing the relationship between the adsorption equilibrium pressure P and the adsorption amount V at that pressure in the adsorption equilibrium state at a constant temperature.

$$(BET \text{ formula}): P/(V(P_0 - P)) = 1/(Vm \times C) + \{((C-1)/(Vm \times C)) \times (P/P_0)\}$$

In the formula, $P_0$: saturated water vapor pressure (Pa), Vm: monomolecular layer adsorption amount (mg/g), C: parameters related to heat of adsorption, etc. (−) <0. This relational equation holds particularly well in the range of $P/P_0$=0.05 to 0.35.

[Measurement of Air Permeability]

150 mm (MD)×150 mm (CD) test pieces were collected from the nonwoven fabric, and the measurement was performed under the condition of a flow rate with a pressure difference of 125 Pa by a Frazier air permeability measuring machine according to JIS L 1096: 2010. The average value of n=5 was regarded as the measured value.

[Measurement of Coating Amount]

The mass of the nonwoven fabric before applying the hydrophilic agent (mass before application) and the mass of the nonwoven fabric after applying and drying the hydrophilic agent (mass after application) were measured, and the coating amount of the hydrophilic agent was calculated by the following formula.

$$\text{Couting Amount}(\%) = [(\text{mass after coating} - \text{mass before coating})/\text{mass after coating}] \times 100$$

[Measurement of Average Crimp Diameter]

The average crimp diameter was measured by the image analysis software "Pixs2000" attached to the optical microscope according to the measurement method described above.

Example 1

(First Layer and Second Layer)

A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C1)") in which the mass ratio of core component/sheath component was 40/60, the first nonwoven web (first layer) and the second nonwoven web (second layer) were formed, and the layered nonwoven web provided with the second nonwoven web on the first nonwoven web was deposited on the movable collecting surface. The crimped composite fibers had an average fiber diameter of 14.2 μm.

—Core Component—

Propylene homopolymer (hPP1) with MFR: 60 g/10 min, and melting point of 162° C.

—Sheath Component—

Propylene/ethylene random copolymer (rPP1) with MFR: 60 g/10 min, melting point of 142° C., and ethylene content of 4% by mass (Third Layer)

A propylene/ethylene random copolymer (rPP1) with MFR: 60 g/10 min, a melting point of 142° C., and an ethylene content of 4% by mass was subjected to melt spinning by the spunbonded method, and the third nonwoven web (third layer) formed of non-crimped type fibers (hereinafter referred to as "non-crimped fibers (NC1)") was layered on the second nonwoven web to form a layered web with a three-layer structure.

The basis weight of the layered web with a three-layer structure is 17 g/m², and the basis weight of each layer was almost equal. Next, the layered web with a three-layer structure was thermocompression bonded at 125° C. so that the embossed roll came into contact with the nonwoven fabric layer side of the first layer, and the mirror surface roll came into contact with the nonwoven fabric layer side of the third layer, and thereby the spunbond nonwoven fabric layered body was obtained. The total basis weight of the spunbond nonwoven fabric layered body was 17 g/m², and the area ratio of the pressure bonding portion was 11%. In the nonwoven fabric layered body of Example 1, the first layer and the second layer correspond to the first nonwoven fabric layer, and the third layer corresponds to the second nonwoven fabric layer.

The following hydrophilic agent A was dissolved in an aqueous solution to obtain an aqueous solution in which the total amount of the active ingredient was diluted to 5%. Next, the obtained spunbond nonwoven fabric layered body was immersed in the aqueous solution of the following hydrophilic agent A, and then the spunbond nonwoven fabric layered body was squeezed. Then, it was dried in a drying oven at 100° C. for 1 minute under a tension of 5 N/m in the MD direction. The physical properties of the spunbond nonwoven fabric layered body (hereinafter referred to as hydrophilic nonwoven fabric layered body) obtained by adhering the hydrophilic agent were measured according to the method described above. The mass of the hydrophilic agent adhering to the hydrophilic nonwoven fabric layered body was determined from the mass difference before and after drying and the concentration of the hydrophilic agent, according to the aforementioned measurement of the coating amount. The coating amount was 0.5% by mass.

(Hydrophilizing Agent A)

Na di(2-ethylhexyl) sulfosuccinate: 20% by mass

Sorbitan lauric acid monoester/sorbitan lauric acid diester/sorbitan lauric acid triester=2:3:5 (mass ratio): 20% by mass Polyoxyethylene monolauric acid ester (8 moles EO chain adduct)/polyoxyethylene lauric acid diester (8 moles EO chain adduct)=4:6 (mass ratio): 30% by mass Polyoxyethylene sorbitan oleic acid monoester (8 moles EO chain adduct)/polyoxyethylene sorbitan oleic acid diester (8 moles EO chain adduct)/polyoxyethylene sorbitan oleic acid triester (8 moles EO chain adduct)=1:6:3 (mass ratio): 30% by mass The above mixing ratio (% by mass) is the ratio of each component with respect to the total mass of the active ingredient in the hydrophilic agent A, that is, in the aqueous solution of the hydrophilic agent A.

Example 2

The hydrophilic nonwoven fabric layered body was obtained in the same manner as in Example 1 except that the coating amount of the hydrophilic agent A was set to 1.0% by mass. In the hydrophilic nonwoven fabric layered body of Example 2, the first layer and the second layer correspond to the first nonwoven fabric layer, and the third layer corresponds to the second nonwoven fabric layer.

Example 3

The hydrophilic nonwoven fabric layered body was obtained in the same manner as in Example 2 except that the total basis weight was 20 g/m². In the hydrophilic nonwoven fabric layered body of Example 3, the first layer and the second layer correspond to the first nonwoven fabric layer, and the third layer corresponds to the second nonwoven fabric layer.

Example 4

The hydrophilic nonwoven fabric layered body was obtained in the same manner as in Example 1 except that the nonwoven fabric layer of the third layer was changed as follows, and the coating amount of the hydrophilic agent A was set to 0.9% by mass. In the hydrophilic nonwoven fabric layered body of Example 4, the first layer and the second layer correspond to the first nonwoven fabric layer, and the third layer corresponds to the second nonwoven fabric layer.
(Third Layer)
A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C2)") in which the mass ratio of core component/sheath component was 85/15, the third nonwoven web (third layer) was deposited on the second nonwoven web (second layer) to form the layered web with a three-layer structure. The crimped composite fibers had an average fiber diameter of 14.7 μm.
—Core Component—
Propylene homopolymer (hPP1) with MFR: 60 g/10 min, and melting point of 162° C.
—Sheath Component—
Propylene/ethylene random copolymer (rPP1) with MFR: 60 g/10 min, melting point of 142° C., and ethylene content of 4% by mass Example 5

The spunbond nonwoven fabric layered body was obtained in the same manner as in Example 2 except that the nonwoven fabric layer of the second layer in Example 1 was not provided with. In other words, the spunbond nonwoven fabric layered body was produced in the same manner as in Example 1, the hydrophilic agent was applied to it in the same manner as in Example 1 except that the second nonwoven web (second layer) was deposited on the first nonwoven web (first layer) to form the layered web with a two layers structure, and thereby the hydrophilic nonwoven fabric layered body was obtained. In the nonwoven fabric layered body of Example 5, the first layer corresponds to the first nonwoven fabric layer, and the second layer corresponds to the second nonwoven fabric layer.

Example 6

The hydrophilic nonwoven fabric layered body was obtained in the same manner as in Example 1 except that the fibers for forming the nonwoven fabric layer of the second layer were changed to the non-crimped fibers (NC1) and the coating amount of the hydrophilic agent A was set to 0.9% by mass. In the hydrophilic nonwoven fabric layered body of Example 6, the first layer corresponds to the first nonwoven fabric layer, and the second layer and the third layer correspond to the second nonwoven fabric layer.

Example 7

The hydrophilic nonwoven fabric layered body was obtained in the same manner as in Example 1 except that the fibers for forming the nonwoven fabric layer of the second layer were changed to the non-crimped fibers (NC1), the fibers for forming the nonwoven fabric layer of the third layer were changed to the crimped fibers (C1), and the coating amount of the hydrophilic agent A was set to 1.10% by mass. In the hydrophilic nonwoven fabric layered body of Example 7, the first layer and the third layer correspond to the first nonwoven fabric layer, and the second layer corresponds to the second nonwoven fabric layer.

Example 8

The spunbond nonwoven fabric layered body was obtained in the same manner as in Example 1 except that the nonwoven fabric layers of the first layer and the second layer were changed as follows, the fibers for forming the nonwoven fabric layer of the third layer were changed to the crimped fibers (C2), the average crimp diameter was changed, and the coating amount of the hydrophilic agent A was set to 0.8% by mass. In the nonwoven fabric layered body of Example 8, the first layer and the second layer correspond to the first nonwoven fabric layer, and the third layer corresponds to the second nonwoven fabric layer.
(First Layer and Second Layer)
A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C3)") in which the mass ratio of core component/sheath component was 60/40, the first nonwoven web (first layer) and the second nonwoven web (second layer) were formed, and the layered nonwoven web provided with the second nonwoven web on the first nonwoven web was deposited on the movable collecting surface. The crimped composite fibers had an average fiber diameter of 14.5 μm.
—Core Component—
Propylene homopolymer (hPP1) with MFR: 60 g/10 min, and melting point of 162° C.
—Sheath Component—
Propylene/ethylene random copolymer (rPP1) with MFR: 60 g/10 min, melting point of 142° C., and ethylene content of 4% by mass Example 9

The spunbond nonwoven fabric layered body was obtained in the same manner as in Example 8 except that the fibers for forming the nonwoven fabric layer of the third layer were changed to the crimped fibers (C4), and the coating amount of the hydrophilic agent A was set to 1.0% by mass. In the nonwoven fabric layered body of Example 9, the first layer and the second layer correspond to the first nonwoven fabric layer, and the third layer corresponds to the second nonwoven fabric layer.

(Third Layer)

A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C4)") in which the mass ratio of core component/sheath component was 80/20, the third nonwoven web (third layer) was deposited on the second nonwoven web (second layer) to form the layered web with a three-layer structure. The crimped composite fibers had an average fiber diameter of 14.3 μm.

—Core Component—

Propylene homopolymer (hPP1) with MFR: 60 g/10 min, and melting point of 162° C.

—Sheath Component—

Propylene/ethylene random copolymer (rPP1) with MFR: 60 g/10 min, melting point of 142° C., and ethylene content of 4% by mass Example 10

The hydrophilic nonwoven fabric layered body was obtained in the same manner as in Example 1 except that thermocompression bonding was performed by embossing so that the area ratio of the pressure bonding portion was 18%. In the hydrophilic nonwoven fabric layered body of Example 10, the first layer corresponds to the first nonwoven fabric layer, and the third layer corresponds to the second nonwoven fabric layer.

Example 11

The hydrophilic nonwoven fabric layered body was obtained in the same manner as in Example 1 except that the first layer and the second layer were changed as follows. In the hydrophilic nonwoven fabric layered body of Example 11, the first layer and the second layer correspond to the first nonwoven fabric layer, and the third layer corresponds to the second nonwoven fabric layer.

(First Layer and Second Layer)

A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C5)") in which the mass ratio of core component/sheath component was 40/60, the first nonwoven web (first layer) and the second nonwoven web (second layer) were formed, and the layered nonwoven web provided with the second nonwoven web on the first nonwoven web was deposited on the movable collecting surface. The crimped composite fibers had an average fiber diameter of 14.3 μm.

—Core Component—

Propylene homopolymer (hPP2) with MFR: 35 g/10 min, and melting point of 160° C.

—Sheath Component—

Mixture including 60% of propylene homopolymer (hPP2) with MFR: 35 g/10 min, and melting point of 160° C. and 40% of propylene/ethylene random copolymer (rPP2) with MFR: 20 g/10 min, and ethylene content of 15% by mass Example 12

The hydrophilic nonwoven fabric layered body was obtained in the same manner as in Example 1 except that the hydrophilic agent A was changed to the following hydrophilic agent B, and the coating amount of the hydrophilic agent B was set to 0.8% by mass. In the hydrophilic nonwoven fabric layered body of Example 12, the first layer and the second layer correspond to the first nonwoven fabric layer, and the third layer corresponds to the second nonwoven fabric layer.

(Hydrophilizing Agent B)

Na di(2-ethylhexyl) sulfosuccinate: 20% by mass

Glycerin oleic acid diester: 30% by mass

Polyoxyethylene glycerin dilauric acid ester/polyoxyethylene glycerin trilauric acid ester=4:6 (mass ratio) (8 moles EO chain adduct): 20% by mass Polyoxyethylene dilauric acid ester (8 moles EO chain adduct): 30% by mass The above mixing ratio (% by mass) is the ratio of each component with respect to the total mass of the active ingredient in the hydrophilic agent B, that is, in the aqueous solution of the hydrophilic agent B.

Example 13

The hydrophilic nonwoven fabric layered body was obtained in the same manner as in Example 12 except that the coating amount of the hydrophilic agent B was set to 1.1% by mass. In the hydrophilic nonwoven fabric layered body of Example 13, the first layer and the second layer correspond to the first nonwoven fabric layer, and the third layer corresponds to the second nonwoven fabric layer.

Example 14

The hydrophilic nonwoven fabric layered body was obtained in the same manner as in Example 1 except that the hydrophilic agent A was changed to the following hydrophilic agent C, and the coating amount of the hydrophilic agent C was set to 1.0% by mass. In the hydrophilic nonwoven fabric layered body of Example 14, the first layer and the second layer correspond to the first nonwoven fabric layer, and the third layer corresponds to the second nonwoven fabric layer.

(Hydrophilizing Agent C)

Na di(2-ethylhexyl) sulfosuccinate: 20% by mass

Glycerin oleic acid diester/glycerin oleic acid triester=5:5 (mass ratio): 50% by mass Polyoxyethylene oleic acid monoester (10 moles EO chain adduct)/polyoxyethylene oleic acid diester (10 moles EO chain adduct)=6:4 (mass ratio): 30 mass %

The above mixing ratio (% by mass) is the ratio of each component with respect to the total mass of the active ingredient in the hydrophilic agent C, that is, in the aqueous solution of the hydrophilic agent C.

Example 15

The spunbond nonwoven fabric layered body was obtained in the same manner as in Example 1 except that the hydrophilic agent A was changed to the following hydrophilic agent D, and the hydrophilic agent D was mixed and spun at a ratio of 1.1% by mass with respect to 100% of the raw material component of the spinning dope of the crimped composite fibers C1. In other words, in the spunbonded fabric layered body of Example 15, the hydrophilic agent A was not applied. In the nonwoven fabric layered body of Example 15, the first layer and the second layer correspond to the first nonwoven fabric layer, and the third layer corresponds to the second nonwoven fabric layer.

(Hydrophilizing Agent D)
Polyoxyethylene (5 moles) stearyl ether: 50% by mass
Polyoxyethylene (10 moles) stearic acid amide: 25% by mass
Glycerin monostearic acid ester: 25% by mass
The above mixing ratio (% by mass) is the ratio of each component with respect to the total mass of the active ingredient in the hydrophilic agent D.

Example 16

The hydrophilic nonwoven fabric layered body was obtained in the same manner as in Example 1 except that the nonwoven fabric layer of the third layer was changed as follows, and the coating amount of the hydrophilic agent A was set to 0.9% by mass. In the hydrophilic nonwoven fabric layered body of Example 16, the first layer and the second layer correspond to the first nonwoven fabric layer, and the third layer corresponds to the second nonwoven fabric layer.
(Third Layer)
A propylene homopolymer (hPP1) with MFR: 60 g/10 min, a melting point of 162° C. was subjected to melt spinning by the spunbonded method, and the third nonwoven web (third layer) formed of non-crimped type fibers (hereinafter referred to as "non-crimped fibers (NC2)") was layered on the second nonwoven web to form a layered web with a three-layer structure.
In a case of comparing Examples with each other on a higher standard, the hydrophilic nonwoven fabric layered body of Example 16 is within a permissible range, but the entanglement due to embossing of the third layer is weaker than that of Examples 1 to 15, and there was concern that the nonwoven fabric was prone to fraying.

Example 17

The hydrophilic nonwoven fabric layered body was obtained in the same manner as in Example 16 except that the embossed thermocompression bonding temperature was set to 130° C. and the coating amount of the hydrophilic agent A was set to 1.0% by mass. In the hydrophilic nonwoven fabric layered body of Example 17, the first layer and the second layer correspond to the first nonwoven fabric layer, and the third layer corresponds to the second nonwoven fabric layer.
In a case of comparing Examples with each other on a higher standard, the hydrophilic nonwoven fabric layered body of Example 17 is within a permissible range, but the emboss portions of the first layer and the second layer became harder and the feel became harder, due to the entanglement by embossing than those of Examples 1 to 15.

Comparative Example 1

The hydrophilic nonwoven fabric layered body was obtained in the same manner as in Example 1 except that the fibers for forming all layers of the first layer to the third layer were changed to the non-crimped fibers (NC2) using hPP1, the total basis weight was changed to 15 g/cm², the temperature of thermocompression bonding was changed to 135° C., and the coating amount of the hydrophilic agent A was set to 1.0% by mass.

Comparative Example 2

The hydrophilic nonwoven fabric layered body was obtained in the same manner as in Comparative Example 1 except that all layers of the first layer to the third layer were changed as follows, the total basis weight was changed to 17 g/cm², and the temperature of thermocompression bonding was changed to 125° C.
(First layer to Third Layer)
A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C6)") in which the mass ratio of core component/sheath component was 90/10, the layered web with a three-layer structure was formed. The crimped composite fibers had an average fiber diameter of 14.2 μm.
—Core Component—
Propylene homopolymer (hPP1) with MFR: 60 g/10 min, and melting point of 162° C.
—Sheath Component—
Propylene/ethylene random copolymer (rPP1) with MFR: 60 g/10 min, melting point of 142° C., and ethylene content of 4% by mass Comparative Example 3

The hydrophilic nonwoven fabric layered body was obtained in the same manner as in Comparative Example 2 except that the coating amount of the hydrophilic agent A was set to 1.5% by mass.

Comparative Example 4

The hydrophilic nonwoven fabric layered body was obtained in the same manner as in Comparative Example 2 except that the third layer was changed to the non-crimped fibers (NC1) as in Example 1.

Example 18

The hydrophilic nonwoven fabric layered body was obtained in the same manner as in Comparative Example 2 except that the fibers for forming all layers of the first layer to the third layer were changed to the crimped fibers (C1).

Comparative Example 5

The hydrophilic nonwoven fabric layered body was obtained in the same manner as in Comparative Example 1 except that the hydrophilic agent A was changed to the hydrophilic agent B, and the coating amount of the hydrophilic agent B was set to 1.10% by mass.

Example 19

(First layer)
A thermoplastic polymer as the following core component and a thermoplastic polymer as the following sheath component were subjected to composite melt spinning by the spunbonded method. Then, from the eccentric core sheath type crimped composite fibers (hereinafter referred to as "crimped fibers (C7)") in which the mass ratio of core component/sheath component was 60/40, the first nonwoven web (first layer) and the second nonwoven web (second layer) were formed, and the layered nonwoven web provided with the second nonwoven web on the first nonwoven web was deposited on the movable collecting surface. The crimped composite fibers had an average fiber diameter of 16.2 μm.

—Core Component—

Propylene homopolymer (hPP1) with MFR: 60 g/10 min, and melting point of 162° C.

—Sheath Component—

Ethylene/1-butene random copolymer (PE1) with MFR: 25 g/10 min, melting point of 115° C., and density of 915 kg/m³

(Second Layer and Third Layer)

The propylene homopolymer (hPP1) as the core component and the ethylene/1-butene random copolymer (PE1) as the sheath component were subjected to composite melt spinning by the spunbonded method. Then, the second nonwoven web (second layer) and the third nonwoven web (third layer) formed of the concentric core sheath type non-crimped composite fibers (hereinafter referred to as "non-crimped fibers (NC3)") in which the mass ratio of core component/sheath component was 75/25 was layered on the first nonwoven web to form a layered web with a three-layer structure.

The basis weight of the layered web with a three-layer structure is 18 g/m², and the basis weight of each layer was almost equal. Next, the layered web with a three-layer structure was thermocompression bonded at 90° C. so that the embossed roll came into contact with the nonwoven fabric layer side of the first layer, and the mirror surface roll came into contact with the nonwoven fabric layer side of the third layer, and thereby the spunbond nonwoven fabric layered body was obtained. The total basis weight of the spunbond nonwoven fabric layered body was 18 g/m², and the area ratio of the pressure bonding portion was 110%. In the nonwoven fabric layered body of Example 19, the first layer corresponds to the first nonwoven fabric layer, and the second layer and the third layer correspond to the second nonwoven fabric layer.

The coating amount of a hydrophilic agent A determined in the same manner as in Example 1 was 1.0% by mass.

Example 20

The spunbond nonwoven fabric layered body was obtained in the same manner as in Example 19 except that, in the eccentric core sheath type crimped composite fibers (hereinafter referred to as "crimped fibers (C8)") of the nonwoven fabric of the first layer in Example 19, the mass ratio of core component/sheath component was 40/60.

Example 21

The spunbond nonwoven fabric layered body was obtained in the same manner as in Example 1 except that the fibers for forming the nonwoven fabric layers of the first layer, the second layer, and the third layer were changed to the crimped fibers (C2), and the coating amount of the hydrophilic agent A was set to 1.0%.

Example 22

The spunbond nonwoven fabric layered body was obtained in the same manner as in Example 1 except that the fibers for forming the nonwoven fabric layers of the first layer, and the second layer were changed to the crimped fibers (C4), the fibers for forming the nonwoven fabric layers of the third layer were changed to the crimped fibers (C2), and the coating amount of the hydrophilic agent A was set to 1.0%.

TABLE 1

| | | Example 1 | Example 2 | Example 3 | Example 4 | Example 5 | Example 6 | Example 7 |
|---|---|---|---|---|---|---|---|---|
| First layer | Core component | hPP1 | hPP1 | hPP1 | hPP1 | hPP1 | hPP1 | hPP1 |
| | Sheath component | rPP1 | rPP1 | rPP1 | rPP1 | rPP1 | rPP1 | rPP1 |
| | Core:Sheath ratio (mass ratio) | 40:60 | 40:60 | 40:60 | 40:60 | 40:60 | 40:60 | 40:60 |
| | Average crimp diameter (m) | 350 | 350 | 350 | 350 | 350 | 350 | 350 |
| Second layer | Core component | hPP1 | hPP1 | hPP1 | hPP1 | rPP1 | rPP1 | rPP1 |
| | Sheath component | rPP1 | rPP1 | rPP1 | rPP1 | — | — | — |
| | Core:Sheath ratio (mass ratio) | 40:60 | 40:60 | 40:60 | 40:60 | — | — | — |
| | Average crimp diameter (m) | 350 | 350 | 350 | 350 | non-crimped | non-crimped | non-crimped |
| Third layer | Core component | rPP1 | rPP1 | rPP1 | hPP1 | — | rPP1 | hPP1 |
| | Sheath component | — | — | — | rPP1 | — | — | rPP1 |
| | Core:Sheath ratio (mass ratio) | — | — | — | 85:15 | — | — | 40:60 |
| | Average crimp diameter (m) | non-crimped | non-crimped | non-crimped | 650 | — | non-crimped | 350 |
| Embossed area ratio (%) | | 11 | 11 | 11 | 11 | 11 | 11 | 11 |
| Embossed thermocompression bonding temperature (° C.) | | 125 | 125 | 125 | 125 | 125 | 125 | 125 |
| Hydrophilizing agent types | | hydrophilic agent A | | | | | | |
| Coating amount (%: to nonwoven fabric layer) | | 0.5 | 1.0 | 1.0 | 0.9 | 1.0 | 0.9 | 1.1 |
| Drying furnace suitability | | A | A | A | A | A | A | A |
| Basis Weight(g/m²) | | 17 | 17 | 20 | 17 | 17 | 17 | 17 |
| Thickness (mm) | | 0.25 | 0.26 | 0.34 | 0.30 | 0.25 | 0.23 | 0.28 |
| MD tensile strength (N/50 mm) | | 16.5 | 17.3 | 19.9 | 15.5 | 19.4 | 21.2 | 18.2 |
| Strength at the time of MD 5% stretching (N/50 mm) | | 2.67 | 2.66 | 3.10 | 2.50 | 3.12 | 3.50 | 2.82 |
| Width retention rate (%) | | 78 | 77 | 80 | 76 | 81 | 82 | 78 |
| WC (g · cm/cm²) | | 0.24 | 0.25 | 0.42 | 0.26 | 0.19 | 0.17 | 0.3 |

TABLE 1-continued

|  | Example 1 | Example 2 | Example 3 | Example 4 | Example 5 | Example 6 | Example 7 |
| --- | --- | --- | --- | --- | --- | --- | --- |
| TO − TM (mm) | 0.31 | 0.32 | 0.45 | 0.35 | 0.28 | 0.27 | 0.38 |
| Cantilever (Flexibility indicator: MD/CD) | 31/15 | 28/15 | 28/15 | 24/13 | 32/16 | 32/17 | 28/14 |
| Liquid flow (45°, 0.1 ml)(mm) | 23 | 20 | 19 | 22 | 23 | 20 | 18 |
| Strike-through 1st (sec) | 0.8 | 0.8 | 0.8 | 1.5 | 0.9 | 1.2 | 1.1 |
| Strike-through 3rd (sec) | 11 | 6.3 | 6.3 | 7 | 6.5 | 5.8 | 6.5 |
| Hydrophilizing agent migration | A | A | A | A | A | A | A |
| Transfer amount of hydrophilic agent to nonwoven fabric transfer target (g/m$^2$) | <0.005 | 0.008 | 0.009 | 0.009 | 0.010 | 0.010 | 0.013 |
| Water vapor adsorption area (m$^2$/g) | 1.25 | 2.00 | 1.80 | 1.70 | 1.75 | 1.60 | 1.90 |
| Water vapor adsorption area/ Nitrogen adsorption area ratio | 5.1 | 8.2 | 7.4 | 7.0 | 7.2 | 6.6 | 7.8 |

TABLE 2

|  |  | Example 8 | Example 9 | Example 10 | Example 11 | Example 12 | Example 13 | Example 14 | Example 15 |
| --- | --- | --- | --- | --- | --- | --- | --- | --- | --- |
| First layer | Core component | hPP1 | hPP1 | hPP1 | hPP2 | hPP1 | hPP1 | hPP1 | hPP1 |
|  | Sheath component | rPP1 | rPP1 | rPP1 | hPP2(60%) + rPP2(40%) | rPP1 | rPP1 | rPP1 | rPP1 |
|  | Core sheath ratio (mass ratio) | 60:40 | 60:40 | 40:60 | 40:60 | 40:60 | 40:60 | 40:60 | 40:60 |
|  | Average crimp diameter (m) | 450 | 450 | 350 | 400 | 350 | 350 | 350 | 350 |
| Second layer | Core component | hPP1 | hPP1 | hPP1 | hPP2 | hPP1 | hPP1 | hPP1 | hPP1 |
|  | Sheath component | rPP1 | rPP1 | rPP1 | hPP2(60%) + rPP2(40%) | rPP1 | rPP1 | rPP1 | rPP1 |
|  | Core sheath ratio (mass ratio) | 60:40 | 60:40 | 40:60 | 40:60 | 40:60 | 40:60 | 40:60 | 40:60 |
|  | Average crimp diameter (m) | 450 | 450 | 350 | 400 | 350 | 350 | 350 | 350 |
| Third layer | Core component | hPP1 | hPP1 | rPP1 | rPP1 | rPP1 | rPP1 | rPP1 | rPP1 |
|  | Sheath component | rPP1 | rPP1 | — | — | — | — | — | — |
|  | Core sheath ratio (mass ratio) | 85:15 | 80:20 | — | — | — | — | — | — |
|  | Average crimp diameter (m) | 650 | 550 | non-crimped | non-crimped | non-crimped | non-crimped | non-crimped | non-crimped |
| Embossed area ratio (%) |  | 11 | 11 | 18 | 11 | 11 | 11 | 11 | 11 |
| Embossed thermocompression bonding temperature (° C.) |  | 125 | 125 | 125 | 125 | 125 | 125 | 125 | 125 |
| Hydrophilizing agent types |  | hydrophilic agent A | | | | hydrophilic agent B | | hydrophilic agent C | hydrophilic agent D |
| Coating amount (%: to nonwoven fabric layer) |  | 0.8 | 1.0 | 0.5 | 0.5 | 0.8 | 1.1 | 1.0 | (kneading amount 1.1) |
| Drying furnace suitability |  | A | A | A | A | A | A | A | A (no drying step) |
| Basis Weight(g/m$^2$) |  | 17 | 17 | 17 | 17 | 17 | 17 | 17 | 17 |
| Thickness (mm) |  | 0.24 | 0.25 | 0.23 | 0.25 | 0.28 | 0.28 | 0.25 | 0.28 |
| MD tensile strength (N/50 mm) |  | 20.6 | 20.0 | 18.5 | 19.0 | 17.0 | 17.6 | 16.8 | 17.1 |
| Strength at the time of MD 5% stretching (N/50 mm) |  | 2.95 | 2.80 | 2.87 | 2.90 | 2.61 | 2.71 | 2.61 | 2.66 |
| Width retention rate (%) |  | 80 | 79 | 82 | 83 | 77 | 76 | 76 | 77 |
| WC (g · cm/cm$^2$) |  | 0.2 | 0.21 | 0.18 | 0.21 | 0.24 | 0.23 | 0.24 | 0.25 |
| TO − TM (mm) |  | 0.28 | 0.28 | 0.25 | 0.28 | 0.3 | 0.29 | 0.31 | 0.33 |
| Cantilever (Flexibility indicator: MD/CD) |  | 32/16 | 33/16 | 33/17 | 30/14 | 25/15 | 27/14 | 30/15 | 26/13 |
| Liquid flow (45°, 0.1 ml)(mm) |  | 17 | 18 | 20 | 25 | 25 | 22 | 23 | 30 |
| Strike-through 1st (sec) |  | 1.3 | 1.1 | 0.8 | 0.9 | 2.3 | 2.1 | 1.1 | 1.8 |
| Strike-through 3rd (sec) |  | 6.8 | 6.0 | 14 | 2.1 | 4 | 3.9 | 2.1 | 2.3 |
| Hydrophilizing agent migration |  | A | A | A | A | A | A | A | A |
| Transfer amount of hydrophilic agent to nonwoven fabric transfer target (g/m$^2$) |  | 0.010 | 0.012 | <0.005 | <0.005 | 0.008 | 0.005 | <0.005 | <0.005 |
| Water vapor adsorption area (m$^2$/g) |  | 1.50 | 1.55 | 1.28 | 1.15 | 1.14 | 1.35 | 1.29 | 0.95 |
| Water vapor adsorption area/ Nitrogen adsorption area ratio |  | 6.1 | 6.4 | 5.2 | 4.7 | 4.7 | 5.5 | 5.3 | 3.9 |

TABLE 3

|  |  | Example 16 | Example 17 | Example 18 | Example 19 | Example 20 | Example 21 | Example 22 |
|---|---|---|---|---|---|---|---|---|
| First layer | Core component | hPP1 | hPP1 | hPP1 | hPP1 | hPP1 | hPP1 | hPP1 |
|  | Sheath component | rPP1 | rPP1 | rPP1 | PE1 | PE1 | rPP1 | rPP1 |
|  | Core sheath ratio (mass ratio) | 40:60 | 40:60 | 40:60 | 60:40 | 40:60 | 85:15 | 80:20 |
|  | Average crimp diameter (m) | 350 | 350 | 350 | 410 | 340 | 650 | 550 |
| Second layer | Core component | hPP1 | hPP1 | hPP1 | hPP1 | hPP1 | hPP1 | hPP1 |
|  | Sheath component | rPP1 | rPP1 | rPP1 | PE1 | PE1 | rPP1 | rPP1 |
|  | Core sheath ratio (mass ratio) | 40:60 | 40:60 | 40:60 | 75:25 | 75:25 | 85:15 | 80:20 |
|  | Average crimp diameter (m) | 350 | 350 | 350 | non-crimped (Concentric) | non-crimped (Concentric) | 650 | 550 |
| Third layer | Core component | hPP1 | hPP1 | hPP1 | hPP1 | hPP1 | hPP1 | hPP1 |
|  | Sheath component | — | — | rPP1 | PE1 | PE1 | rPP1 | rPP1 |
|  | Core sheath ratio (mass ratio) | — | — | 40:60 | 75:25 | 75:25 | 85:15 | 85:15 |
|  | Average crimp diameter (m) | non-crimped | non-crimped | 350 | non-crimped (Concentric) | non-crimped (Concentric) | 650 | 650 |
| Embossed area ratio (%) |  | 11 | 11 | 11 | 11 | 11 | 11 | 11 |
| Embossed thermocompression bonding temperature (° C.) |  | 125 | 130 | 125 | 90 | 90 | 125 | 125 |
| Hydrophilizing agent types |  | hydrophilic agent A |  |  |  |  |  |  |
| Coating amount (%: to nonwoven fabric layer) |  | 0.9 | 1.0 | 1.0 | 1.0 | 1.0 | 1.0 | 1.0 |
| Drying furnace suitability |  | A | A | B | A | A | A | A |
| Basis Weight(g/m$^2$) |  | 17 | 17 | 17 | 18 | 18 | 17 | 17 |
| Thickness (mm) |  | 0.25 | 0.27 | 0.36 | 0.25 | 0.25 | 0.21 | 0.23 |
| MD tensile strength (N/50 mm) |  | 14.7 | 17.3 | 13.8 | 16.7 | 15.0 | 22.5 | 21.7 |
| Strength at the time of MD 5% stretching (N/50 mm) |  | 2.26 | 2.69 | 2.12 | 3.20 | 3.02 | 4.88 | 4.21 |
| Width retention rate (%) |  | 76 | 78 | 73 | 80 | 79 | 84 | 82 |
| WC (g · cm/cm$^2$) |  | 0.25 | 0.24 | 0.44 | 0.18 | 0.19 | 0.17 | 0.19 |
| TO – TM (mm) |  | 0.31 | 0.30 | 0.45 | 0.26 | 0.28 | 0.20 | 0.23 |
| Cantilever (Flexibility indicator: MD/CD) |  | 28/15 | 33/16 | 22/12 | 31/15 | 28/15 | 33/18 | 33/17 |
| Liquid flow (45°, 0.1 ml)(mm) |  | 23 | 21 | 22 | 21 | 20 | 21 | 20 |
| Strike-through 1st (sec) |  | 0.8 | 1.7 | 1.8 | 1.1 | 0.9 | 1.8 | 1.9 |
| Strike-through 3rd (sec) |  | 14 | 7.1 | 6 | 5.9 | 6.5 | 5.6 | 5.9 |
| Hydrophilizing agent migration |  | A | A | A | A | A | A~B | A |
| Transfer amount of hydrophilic agent to nonwoven fabric transfer target (g/m$^2$) |  | 0.010 | 0.012 | 0.013 | 0.011 | 0.01 | 0.016 | 0.015 |
| Water vapor adsorption area (m$^2$/g) |  | 1.65 | 1.92 | 2.10 | 1.75 | 2.00 | 1.88 | 1.82 |
| Water vapor adsorption area/ Nitrogen adsorption area ratio |  | 6.8 | 7.9 | 8.6 | 7.2 | 8.2 | 7.7 | 7.5 |

TABLE 4

|  |  | Comparative Example 1 | Comparative Example 2 | Comparative Example 3 | Comparative Example 4 | Comparative Example 5 |
|---|---|---|---|---|---|---|
| First layer | Core component | hPP1 | hPP1 | hPP1 | hPP1 | hPP1 |
|  | Sheath component | — | rPP1 | rPP1 | rPP1 | — |
|  | Core sheath ratio (mass ratio) | — | 90:10 | 90:10 | 90:10 | — |
|  | Average crimp diameter (m) | non-crimped | 900 | 900 | 900 | non-crimped |
| Second layer | Core component | hPP1 | hPP1 | hPP1 | hPP1 | hPP1 |
|  | Sheath component | — | rPP1 | rPP1 | rPP1 | — |
|  | Core sheath ratio (mass ratio) | — | 90:10 | 90:10 | 90:10 | — |
|  | Average crimp diameter (m) | non-crimped | 900 | 900 | 900 | non-crimped |
| Third layer | Core component | hPP1 | hPP1 | hPP1 | rPP1 | hPP1 |
|  | Sheath component | — | rPP1 | rPP1 | — | — |
|  | Core sheath ratio (mass ratio) | — | 90:10 | 90:10 | — | — |
|  | Average crimp diameter (m) | non-crimped | 900 | 900 | non-crimped | non-crimped |

TABLE 4-continued

|  | Comparative Example 1 | Comparative Example 2 | Comparative Example 3 | Comparative Example 4 | Comparative Example 5 |
|---|---|---|---|---|---|
| Embossed area ratio (%) | 11 | 11 | 11 | 11 | 11 |
| Embossed thermocompression bonding temperature (° C.) | 135 | 125 | 125 | 125 | 125 |
| Hydrophilizing agent types | | hydrophilic agent A | | | Hydrophilizing agent B |
| Coating amount (%: to nonwoven fabric layer) | 1.0 | 1.0 | 1.5 | 1 | 1.1 |
| Drying furnace suitability | A | A | A | A | A |
| Basis Weight(g/m$^2$) | 15 | 17 | 17 | 17 | 15 |
| Thickness (mm) | 0.19 | 0.22 | not evaluated | 0.21 | 0.20 |
| MD tensile strength (N/50 mm) | 26.4 | 23.5 | not evaluated | 24.9 | 27.1 |
| Strength at the time of MD 5% stretching (N/50 mm) | 7.95 | 5.45 | not evaluated | 6.70 | 7.42 |
| Width retention rate (%) | 90 | 85 | not evaluated | 88 | 92 |
| WC (g · cm/cm$^2$) | 0.12 | 0.16 | not evaluated | 0.14 | 0.11 |
| TO – TM (mm) | 0.10 | 0.19 | not evaluated | 0.15 | 0.09 |
| Cantilever (Flexibility indicator: MD/CD) | 40/25 | 35/20 | not evaluated | 38/23 | 41/26 |
| Liquid flow (45°, 0.1 ml)(mm) | 21 | 21 | 19 | 21 | 24 |
| Strike-through 1st (sec) | 1.8 | 1.8 | 0.8 | 1.8 | 1.8 |
| Strike-through 3rd (sec) | 5.5 | 5.7 | 4.5 | 5.6 | 3.6 |
| Hydrophilizing agent migration | C | B | C | B | C |
| Transfer amount of hydrophilic agent to nonwoven fabric transfer target (g/m$^2$) | 0.031 | 0.016 | 0.043 | 0.018 | 0.028 |
| Water vapor adsorption area (m$^2$/g) | 1.71 | 1.90 | 2.60 | 1.80 | 1.82 |
| Water vapor adsorption area/ Nitrogen adsorption area ratio | 5.4 | 7.8 | 10.7 | 7.4 | 5.8 |

From the results of Tables 1 to 4 above, it was confirmed that the nonwoven fabric layered bodies of Examples are more excellent in hydrophilicity, more suppresses the migration of a hydrophilic agent when it comes into contact with another member, and has more excellent dimensional stability than the nonwoven fabric layered bodies of Comparative Examples.

Examples 23 to 33

(First Layer and Second Layer)

First, the layered nonwoven web provided with the second nonwoven web (second layer, layer of spunbond nonwoven fabric) on the first nonwoven web (first layer, layer of spunbond nonwoven fabric) was deposited on the movable collecting surface in the same manner as in Example 1.

(Third Layer)

Next, using the polymers of MB1 to MB5 shown below, the molten polymer was discharged from a spinneret having nozzles of 0.38 mmφ to perform melt spinning by the melt-blown method, and the fibers were deposited on the second nonwoven web in the aforementioned layered nonwoven web. As a result, the layered web in which the melt-blown webs (third layer, MB) having the basis weight shown in Table 5 were formed on the second non-woven web (second layer, layer of spunbond nonwoven fabric) was formed. As shown in Table 5, in Example 27 and Example 28, polymers in which MB1 and MB2 were mixed at a mass ratio of 90/10 or 80/20 (MB1/MB2) were used, in Example 29 and Example 30, polymers in which MB3, MB2 and MB4 were mixed at a mass ratio of 40/20/40 (MB3/MB2/MB4) were used, in Example 31, polymers in which MB3 and MB2 were mixed at a mass ratio of 60/40 (MB3/MB2) were used, and in Example 32, polymers in which MB2 and MB4 were mixed at a mass ratio of 60/40 (MB2/MB4) were used. The spinning temperature in each Example was 245° C. for MB1 of Examples 23 to 26, 250° C. for the polymers obtained by mixing MB1 and MB2 of Example 27 and Example 28, 290° C. for the polymers obtained by mixing MB3, MB2 and MB4 of Example 29 and Example 30, 300° C. for the polymers obtained by mixing MB3 and MB2 of Example 31, 300° C. for the polymers obtained by mixing MB2 and MB4 of Example 32, and 300° C. for MB5 of Example 33.

MB1: Polypropylene homopolymer (MFR: 1,100 g/10 min, weight average molecular weight (Mw): 97,000)

MB2: Propylene/ethylene copolymer [manufactured by ExxonMobil Corporation: product name "Vistamaxx™6202", MFR (230° C., 2,160 g load): 20 g/10 min, ethylene content: 15% by mass]

MB3: Propylene homopolymer [MFR: 1,500 g/10 min, weight average molecular weight (Mw): 54000]

MB4: Propylene polymer wax [Density: 0.900 g/cm$^3$, weight average molecular weight: 7,800, softening point 148° C., ethylene content: 1.7% by mass]

MB5: Propylene-ethylene random copolymer (rPP1) according to Example 1.

(Fourth Layer)

Next, the third nonwoven web (third layer, layer of spunbond nonwoven fabric) was layered on the melt-blown web in the same manner as in Example 1 to form a layered web with a four-layer structure.

The basis weight of the layered web with a four-layer structure excluding the third layer is 17 g/m$^2$. Next, the layered web with a four-layer structure was thermocompression bonded at 125° C. so that the embossed roll came into contact with the nonwoven fabric layer side of the first layer, and the mirror surface roll came into contact with the nonwoven fabric layer side of the fourth layer, and thereby the nonwoven fabric layered body was obtained. The area ratio of the pressure bonding portion was 11%. In the nonwoven fabric layered bodies of Examples 23 to 33, the first layer and the second layer correspond to the first nonwoven fabric layer, and the fourth layer corresponds to the second nonwoven fabric layer. Further, the hydrophilic agent was adhered to the nonwoven fabric layered body as in Example 1. The mass of the hydrophilic agent adhering to the nonwoven fabric layered body was determined from the mass difference before and after drying and the concentration of the hydrophilic agent, according to the aforementioned measurement of the coating amount. The coating amount was 0.5% by mass.

TABLE 5

| | | Example 23 | Example 24 | Example 25 | Example 26 | Example 27 | Example 28 |
|---|---|---|---|---|---|---|---|
| SB first layer | Core component | hPP1 | hPP1 | hPP1 | hPP1 | hPP1 | hPP1 |
| | Sheath component | rPP1 | rPP1 | rPP1 | rPP1 | rPP1 | rPP1 |
| | Core sheath ratio (mass ratio) | 40:60 | 40:60 | 40:60 | 40:60 | 40:60 | 40:60 |
| | Crimped or non-Crimped | crimped | crimped | crimped | crimped | crimped | crimped |
| | Average crimp diameter (m) | 350 | 350 | 350 | 350 | 350 | 350 |
| SB second layer | Core component | hPP1 | hPP1 | hPP1 | hPP1 | hPP1 | hPP1 |
| | Sheath component | rPP1 | rPP1 | rPP1 | rPP1 | rPP1 | rPP1 |
| | Core sheath ratio (mass ratio) | 40:60 | 40:60 | 40:60 | 40:60 | 40:60 | 40:60 |
| | Crimped or non-Crimped | crimped | crimped | crimped | crimped | crimped | crimped |
| | Average crimp diameter (m) | 350 | 350 | 350 | 350 | 350 | 350 |
| MB third layer | Raw material 1 | MB1 | MB1 | MB1 | MB1 | MB1 | MB1 |
| | Raw material 2 | — | — | — | — | MB2 | MB2 |
| | Raw material 3 | — | — | — | — | — | — |
| | Raw material mixing ratio (mass ratio) | — | — | — | — | 90/10 | 80/20 |
| | Raw material MFR (g/m$^2$) | 850 | 850 | 850 | 850 | 740 | 500 |
| | Propene ratio (%) | 100 | 100 | 100 | 100 | 98.5 | 97 |
| | Average crimp diameter (m) | 1.43 | 1.52 | 1.65 | 1.55 | 1.82 | 1.93 |
| SB fourth layer | Core component | rPP1 | rPP1 | rPP1 | rPP1 | rPP1 | rPP1 |
| | Sheath component | — | — | — | — | — | — |
| | Core sheath ratio (mass ratio) | — | — | — | — | — | — |
| | Crimped or non-Crimped | non-crimped | non-crimped | non-crimped | non-crimped | non-crimped | non-crimped |
| | Average crimp diameter (m) | non-crimped | non-crimped | non-crimped | non-crimped | non-crimped | non-crimped |
| Embossed area ratio (%) | | 11 | 11 | 11 | 11 | 11 | 11 |
| Embossed thermocompression bonding temperature (° C.) | | 125 | 125 | 125 | 125 | 125 | 125 |
| Hydrophilizing agent types | | | | hydrophilic agent A | | | |
| Coating amount (%: to nonwoven fabric layer) | | 0.5 | 0.5 | 0.5 | 0.5 | 0.5 | 0.5 |
| Drying furnace suitability | | A | A | A | A | A | A |
| Basis Weight (g/m$^2$) | | 17 | 17 | 17 | 17 | 17 | 17 |
| Basis Weight of MD layer (g/m$^2$) | | 0.85 | 1 | 2 | 4 | 1 | 1 |
| Thickness (mm) | | 0.25 | 0.26 | 0.28 | 0.23 | 0.25 | 0.26 |
| MD tensile strength (N/50 mm) | | 16.3 | 15.5 | 14.7 | 12.5 | 15.2 | 15.1 |
| Strength at the time of MD 5% stretching (N/50 mm) | | 2.60 | 2.48 | 2.42 | 2.45 | 2.45 | 2.43 |
| Width retention rate (%) | | 78 | 78 | 79 | 82 | 77 | 76 |
| WC (g · cm/cm$^2$) | | 0.23 | 0.23 | 0.21 | 0.19 | 0.23 | 0.22 |
| TO – TM (mm) | | 0.36 | 0.36 | 0.33 | 0.28 | 0.37 | 0.36 |
| Cantilever (Flexibility indicator: MD/CD) | | 24/20 | 25/19 | 26/22 | 28/24 | 22/18 | 21/17 |
| Liquid flow (45°, 0.1 ml)(mm) | | 23 | 23 | 22 | 24 | 25 | 22 |
| Strike-through 1 st (sec) | | 1.8 | 1.7 | 2 | 2.2 | 1.7 | 1.6 |
| Strike-through 3rd (sec) | | 20 | 19 | 22 | 24 | 9.9 | 7.8 |
| Hydrophilizing agent migration | | A | A | A | A | A | A |
| Transfer amount of hydrophilic agent to nonwoven fabric transfer target (g/m$^2$) | | <0.005 | <0.005 | <0.005 | 0.007 | <0.005 | <0.005 |
| Air permeability (cm$^3$/cm$^2$/sec) | | 229 | 207 | 158 | 87 | 225 | 232 |

| | | | Example 29 | Example 30 | Example 31 | Example 32 | Example 33 |
|---|---|---|---|---|---|---|---|
| | SB first layer | Core component | hPP1 | hPP1 | hPP1 | hPP1 | hPP1 |
| | | Sheath component | rPP1 | rPP1 | rPP1 | rPP1 | rPP1 |
| | | Core sheath ratio (mass ratio) | 40:60 | 40:60 | 40:60 | 40:60 | 40:60 |
| | | Crimped or non-Crimped | crimped | crimped | crimped | crimped | crimped |
| | | Average crimp diameter (m) | 350 | 350 | 350 | 350 | 350 |
| | SB second layer | Core component | hPP1 | hPP1 | hPP1 | hPP1 | hPP1 |
| | | Sheath component | rPP1 | rPP1 | rPP1 | rPP1 | rPP1 |
| | | Core sheath ratio (mass ratio) | 40:60 | 40:60 | 40:60 | 40:60 | 40:60 |

TABLE 5-continued

|  |  |  |  |  |  |  |
|---|---|---|---|---|---|---|
| | Crimped or non-Crimped | crimped | crimped | crimped | crimped | crimped |
| | Average crimp diameter (m) | 350 | 350 | 350 | 350 | 350 |
| MB third layer | Raw material 1 | MB3 | MB3 | MB3 | MB2 | MB5 |
| | Raw material 2 | MB2 | MB2 | MB2 | MB4 | — |
| | Raw material 3 | MB4 | MB4 | — | — | — |
| | Raw material mixing ratio (mass ratio) | 40/20/40 | 40/20/40 | 60/40 | 60/40 | — |
| | Raw material MFR (g/m²) | 460 | 460 | 270 | 220 | 60 |
| | Propene ratio (%) | 93.3 | 93.3 | 94 | 90.3 | 97 |
| | Average crimp diameter (m) | 1.95 | 1.95 | 2.1 | 2.45 | 3.2 |
| SB fourth layer | Core component | rPP1 | rPP1 | rPP1 | rPP1 | rPP1 |
| | Sheath component | — | — | — | — | — |
| | Core sheath ratio (mass ratio) | — | — | — | — | — |
| | Crimped or non-Crimped | non-crimped | non-crimped | non-crimped | non-crimped | non-crimped |
| | Average crimp diameter (m) | non-crimped | non-crimped | non-crimped | non-crimped | non-crimped |
| Embossed area ratio (%) | | 11 | 11 | 11 | 11 | 11 |
| Embossed thermocompression bonding temperature (° C.) | | 125 | 125 | 125 | 125 | 125 |
| Hydrophilizing agent types | | hydrophilic agent A | | | | |
| Coating amount (%: to nonwoven fabric layer) | | 0.5 | 0.5 | 0.5 | 0.5 | 0.5 |
| Drying furnace suitability | | A | A | A | A | A |
| Basis Weight(g/m²) | | 17 | 17 | 17 | 17 | 17 |
| Basis Weight of MD layer (g/m²) | | 1 | 2 | 1 | 1 | 1 |
| Thickness (mm) | | 0.26 | 0.25 | 0.25 | 0.26 | 0.23 |
| MD tensile strength (N/50 mm) | | 15.3 | 14.3 | 16.2 | 15.6 | 16.5 |
| Strength at the time of MD 5% stretching (N/50 mm) | | 2.35 | 2.2 | 2.59 | 2.48 | 2.67 |
| Width retention rate (%) | | 77 | 76 | 79 | 76 | 78 |
| WC (g · cm/cm²) | | 0.24 | 0.20 | 0.26 | 0.31 | 0.23 |
| TO – TM (mm) | | 0.36 | 0.34 | 0.35 | 0.29 | 0.34 |
| Cantilever (Flexibility indicator: MD/CD) | | 22/17 | 24/21 | 20/16 | 20/17 | 22/17 |
| Liquid flow (45°, 0.1 ml)(mm) | | 23 | 23 | 19 | 25 | 21 |
| Strike-through 1 st (sec) | | 1.5 | 1.7 | 1.6 | 1.4 | 1.7 |
| Strike-through 3rd (sec) | | 6.7 | 12 | 8.7 | 7.2 | 5.5 |
| Hydrophilizing agent migration | | A | A | A | A | A |
| Transfer amount of hydrophilic agent to nonwoven fabric transfer target (g/m²) | | <0.005 | 0.006 | <0.005 | <0.005 | <0.005 |
| Air permeability (cm³/cm²/sec) | | 228 | 210 | 226 | 265 | 250 |

From the results of Table 5 above, it was confirmed that the nonwoven fabric layered bodies of Examples are excellent in hydrophilicity, suppresses the migration of a hydrophilic agent when it comes into contact with another member, and has excellent dimensional stability. Further, as shown in Table 5, flexibility was ensured even in an aspect in which the layer of spunbond nonwoven fabric and the melt-blown nonwoven fabric layer were layered.

The disclosure of Japanese Patent Application 2019-42943, filed on Mar. 8, 2019 and Japanese Patent Application 2019-196708, filed on Oct. 29, 2019 are incorporated herein by reference in their entirety.

All publications, patent applications, and technical standards mentioned in the present specification are incorporated herein by reference to the same extent as if each individual publication, patent application, or technical standard was specifically and individually indicated to be incorporated by reference.

The invention claimed is:

1. A nonwoven fabric layered body, comprising:
a first nonwoven fabric layer including a crimped fiber (A), which is a fiber made of a thermoplastic polymer and which has an average crimp diameter of 800 μm or less;
a hydrophilic agent; and
a melt-blown nonwoven fabric layer comprising a fiber made of a thermoplastic polymer;
wherein the thermoplastic polymer in the melt-blown nonwoven fabric layer is a propylene homopolymer having a melt flow rate of 800 g/10 min or more, an average fiber diameter of the fiber in the melt-blown nonwoven fabric layer is less than 3 μm, and a basis weight of the melt-blown nonwoven fabric layer is less than 3 g/m².

2. The nonwoven fabric layered body according to claim 1, wherein the thermoplastic polymer in the melt-blown nonwoven fabric layer is a propylene/α-olefin copolymer having a melt flow rate of 200 g/10 min or more, or a mixture of a propylene polymer comprising a propylene/α-olefin copolymer, and a basis weight of the melt-blown nonwoven fabric layer is less than 5 g/m².

3. A composite layered body, comprising the nonwoven fabric layered body according to claim 1.

4. A cover sheet, comprising the nonwoven fabric layered body according to claim 1.

5. The nonwoven fabric layered body according to claim 1, wherein the nonwoven fabric layered body satisfies following (1) or (2), (1) the nonwoven fabric layer body includes a second nonwoven fabric layer including a crimped fiber (B), which is a fiber made of a thermoplastic polymer and which has a different average crimp diameter from the average crimp diameter of the crimped fiber (A), the average crimp diameter of the crimped fiber (B) being 500 μm or more, or a non-crimped fiber (C), which is a fiber made of a thermoplastic polymer, the fiber of the thermoplastic polymer included in the first nonwoven fabric layer and the second nonwoven fabric comprises a propylene polymer, the propylene polymer is exposed at a surface of the crimped fiber (A) included in the first nonwoven fabric layer, the propylene polymer is exposed at a surface of the crimped fiber (B) or the noncrimped fiber (C) included in the second nonwoven fabric layer, and a difference in a melting point between the propylene polymer exposed at the surface of the crimped fiber (A) and the propylene polymer exposed at the surface of the crimped fiber (B) or the non-crimped fiber (C) is from −15° C. to +15° C.;

(2) the nonwoven fabric layer body includes a second nonwoven fabric layered body including a non-crimped fiber (C), which includes an ethylene polymer, the non-crimped fiber (C) includes a core portion and a sheath portion, and a mass ratio of the sheath portion and the core portion (core portion/sheath portion) is from 95/5 to 75/25.

6. The nonwoven fabric layered body according to claim 1, wherein the first nonwoven fabric layer is an outermost layer, and the average crimp diameter of the crimped fiber (A) is 600 μm or less.

7. The nonwoven fabric layered body according to claim 5, wherein in the case of the (2), the thermoplastic polymer in the crimped fiber (A) comprises an olefin polymer.

8. The nonwoven fabric layered body according to claim 7, wherein in the case of the (2), the thermoplastic polymer in the crimped fiber (A) comprises at least one selected from the group consisting of a propylene polymer and an ethylene polymer as the olefin polymer.

9. The nonwoven fabric layered body according to claim 1, wherein a width retention rate is 75% or more in a case in which a tensile stress of 0.1 N/mm is applied in an MD direction of the nonwoven fabric layered body.

10. The nonwoven fabric layered body according to claim 1, wherein a tensile strength at the time of 5% stretching in an MD direction of the nonwoven fabric layered body is 2.2 N/50 mm or more.

11. The nonwoven fabric layered body according to claim 1, wherein a transfer amount of the hydrophilic agent from the nonwoven fabric layered body to a nonwoven fabric transfer target is 0.015 g/m² or less.

12. The nonwoven fabric layered body according to claim 1, wherein a ratio (surface water vapor adsorption area/surface nitrogen adsorption area) of a surface water vapor adsorption area obtained by a BET formula of a water vapor adsorption isotherm in a water vapor adsorption test, with respect to a surface nitrogen adsorption area obtained by a BET formula of a nitrogen adsorption isotherm in a nitrogen adsorption test, is from 1.5 to 9.0.

13. The nonwoven fabric layered body according to claim 1, wherein the hydrophilic agent comprises at least one selected from the group consisting of a polyhydric alcohol fatty acid ester, a polyoxyalkylene fatty acid ester, and an alkylene oxide adduct of a polyhydric alcohol fatty acid ester.

14. The nonwoven fabric layered body according to claim 5, wherein in the case of the (1), the second nonwoven fabric layer comprises the non-crimped fiber (C).

15. The nonwoven fabric layered body according to claim 5, wherein in the case of the (1), the propylene polymer exposed at the surface of the crimped fiber (A) and the propylene polymer exposed at the surface of the crimped fiber (B) or the non-crimped fiber (C) are respectively a propylene/α-olefin copolymer, a mixture of a propylene homopolymer and a propylene/α-olefin copolymer, or a combination thereof.

16. The nonwoven fabric layered body according to claim 1, wherein the first nonwoven fabric layer is a layer of a spunbond nonwoven fabric, the second nonwoven fabric layer is a layer of a spunbond nonwoven fabric, the nonwoven fabric layered body has a pressure bonding portion and a non-pressure bonding portion, and an area ratio of the pressure bonding portion is from 7% to 20%.

* * * * *